United States Patent [19]

Wissner et al.

[11] 4,288,633
[45] Sep. 8, 1981

[54] 1-HYDROXYMETHYL-11-DEOXY-16-HYDROXY-PROSTEN-1-OL-DERIVATIVES

[75] Inventors: Allan Wissner, Ardsley; Middleton B. Floyd, Jr., Suffern, both of N.Y.

[73] Assignee: American Cyanamid Company, Stamford, Conn.

[21] Appl. No.: 137,031

[22] Filed: Apr. 3, 1980

[51] Int. Cl.³ .................. C07C 35/06; C07C 49/597
[52] U.S. Cl. .................. 568/367; 568/379; 568/664; 568/669; 568/670; 568/816; 568/838; 560/231; 560/64; 560/65; 560/73; 560/106; 560/107; 424/308; 424/311; 424/331; 424/341; 424/339; 424/343; 568/376; 568/631; 568/644; 568/645; 568/807; 568/822; 568/380
[58] Field of Search .............. 568/367, 379, 380, 664, 568/669, 670, 838, 822, 331, 644, 645, 807, 816, 330; 560/231, 64, 65, 73, 106, 107, 255, 61, 62, 63; 424/308, 311, 343, 331, 340, 341, 339

[56] References Cited

U.S. PATENT DOCUMENTS

| | | | |
|---|---|---|---|
| 3,873,607 | 3/1975 | Bernady et al. | 560/51 |
| 3,931,289 | 1/1976 | Bundy | 560/53 |
| 3,936,487 | 2/1976 | Nelson | 560/231 |
| 3,944,593 | 3/1976 | Nelson | 560/231 |
| 3,950,406 | 4/1976 | Floyd et al. | 560/51 |
| 3,965,143 | 6/1976 | Collins et al. | 560/121 |
| 4,061,670 | 12/1977 | Floyd et al. | 560/37 |
| 4,212,969 | 7/1980 | Wissner et al. | 560/231 |

FOREIGN PATENT DOCUMENTS 827127 11/1976 Belgium .
7305222 7/1978 Netherlands .

OTHER PUBLICATIONS

Bently, Chem. Soc. Rev., #2, pp. 29–70, (1973).

*Primary Examiner*—Natalie Trousof
*Assistant Examiner*—James H. Reamer
*Attorney, Agent, or Firm*—Norton S. Johnson

[57] ABSTRACT

Prostaglandin analogs are disclosed that have the α-chain terminating with the group —CH(OR')OR" wherein R' and R" are the same or different and are hydrogen, $C_1$ to $C_4$ alkanoyl or optionally substituted benzoyl, the substituents selected from the group $C_1$ to $C_4$ alkyl, $C_1$ to $C_4$ alkoxy, halo and trifluoromethyl. These compounds are useful as hypotensive agents, gastric secretory and platelet aggregation inhibitors and bronchodilators.

52 Claims, No Drawings

1-HYDROXYMETHYL-11-DEOXY-16-HYDROXY-PROSTEN-1-OL-DERIVATIVES

BACKGROUND OF THE INVENTION (1) Field of the Invention

The present invention relates to 1-hydroxy-1-hydroxymethyl prostaglandins, as well as the pharmaceutically acceptable, non-toxic $C_1$ to $C_4$ alkyl esters thereof, and to the intermediates and processes for producing such compounds.

(2) Description of the Prior Art

Prostaglandins have classically been described as chemically related 20 carbon chain hydroxy fatty acids having the basic skeleton of prostanoic acid:

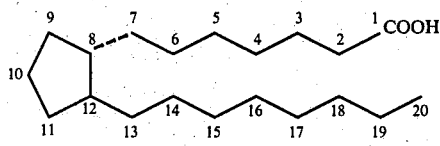

The prostaglandins having a hydroxyl group at the C-11 position and a keto group at the C-9 position are known as the PGE series, and those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example P. Ramwell, *The Prostaglandins*, 1, pp. 5-22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al., *Synthesis* Vol. 1, John Wiley and Sons Inc., New York, N. Y. 1973 and P. H. Bently, *Chem. Soc. Reviews* 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared [see for example, U.S. Pat. No. 3,950,406; *Prostaglandins*, Vol. 10, 733 (1975); *Tetrahedron Letters*, No. 48, 4217 (1975)].

Recently reports have also appeared wherein the C-16 carbon bearing a hydroxyl group is substituted with a methyl group [see Pappo et al., *Tetrahedron Letters*, No. 4, 235 (1975); Collin et al., U.S. Pat. No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670).

SUMMARY

Compounds of the formula:

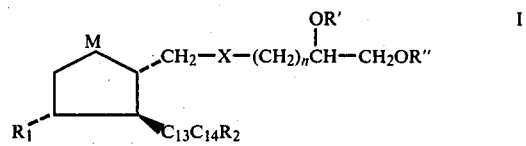

wherein n is the integer 3-5 inclusive; M is the divalent moiety selected from the group

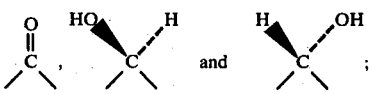

X is selected from the group —$CH_2CH_2$—, —CH=CH—(trans) and —CH=CH—(cis); R' and R" are the same or different and are hydrogen, $C_1$ to $C_4$ alkyl, $C_1$ to $C_6$ alkanoyl or optionally substituted benzoyl, the substituents selected from the group $C_1$ to $C_4$ alkyl, $C_1$ to $C_4$ alkoxy, halo and trifluoromethyl; $R_1$ is hydrogen or hydroxy; $C_{13}$-$C_{14}$ is selected from the group —CH=CH—(trans) and —$CH_2CH_2$—; and $R_2$ is selected from the group

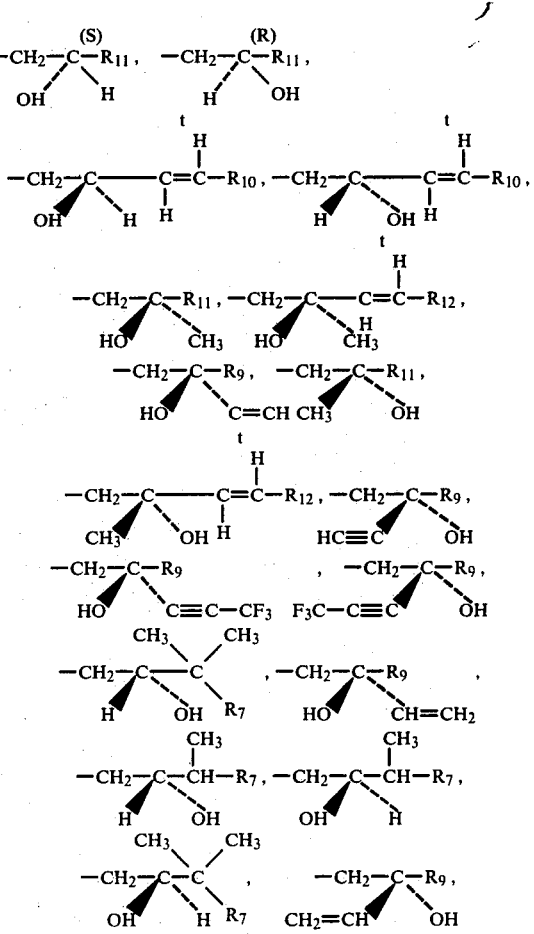

-continued

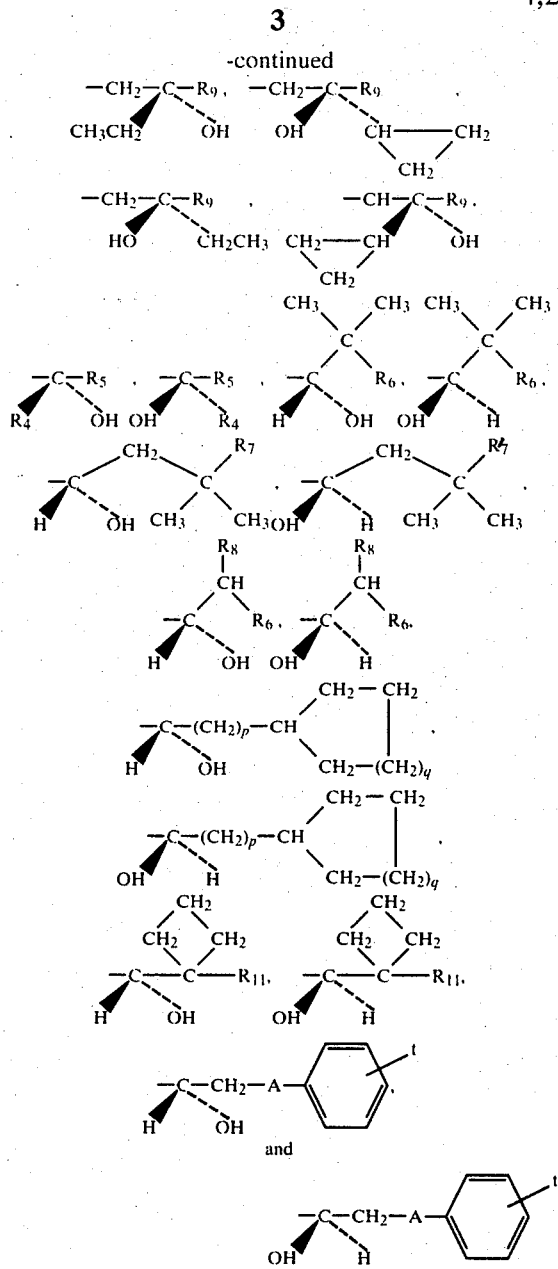

wherein $R_4$ is hydrogen, vinyl or methyl; $R_5$ is selected from the group consisting of $C_4$–$C_7$ alkyl; $R_6$ is selected from the group consisting of $C_3$–$C_6$ alkyl; $R_7$ is selected from the group consisting of $C_2$–$C_4$ alkyl; $R_8$ is selected from the group consisting of $C_1$–$C_2$ alkyl; $R_9$ is selected from the group consisting of $C_3$–$C_6$ alkyl; $R_{10}$ is selected from the group consisting of $C_1$–$C_4$ alkyl; $R_{11}$ is selected from the group consisting of $C_3$–$C_7$ alkyl; $R_{12}$ is selected from the group consisting of $C_1$–$C_4$ alkyl; p is an integer from 0 to 3; q is 1 or 2; A is a divalent radical selected from —$CH_2$ and —O—; s is the integer 0 or 1; and t is selected from the group consisting of hydrogen, chloro, fluoro, dichloro, trifluoromethyl, and methoxy; the racemic mixtures thereof; and the individual optically active enantiomers thereof.

The compounds of this invention can be prepared by a 1,4-conjugate-addition procedure involving treatment of an ether blocked cyclopentenone with a lithiocuprate reagent. These processes and many of the intermediates useful for the preparation of the compounds of formula I are set forth in some detail in U.S. Application Ser. No. 3,953, filed Jan. 16, 1979, incorporated herein by reference.

DESCRIPTION OF THE PREFERRED EMBODIMENTS

The prostaglandin compounds of the present invention of formula I may subgenerically be represented by the compounds of the following formulas:

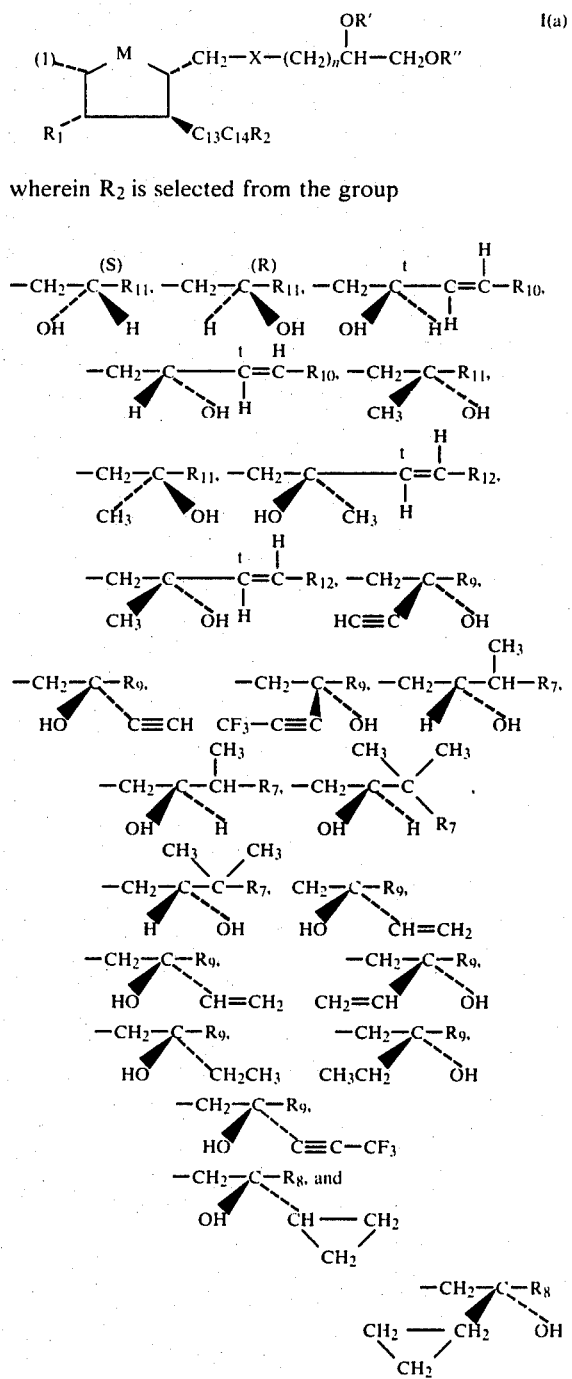

wherein n, R, R″, $R_1$, $R_7$, $R_8$, $R_9$, $R_{10}$, $R_{11}$, $R_{12}$, M, X and $C_{13}$–$C_{14}$ are as previously defined.

In the above compounds of formula I(a) it is preferred that:

X is selected from the group —CH₂CH₂— and —CH=CH—(cis), most preferably —CH=CH—(cis); R' and R" are the same or different and are hydrogen or C₁ to C₄ alkanoyl, most preferably the same and are hydrogen; C₁₃C₁₄ is —CH=CH—(trans); and R₂ is selected from the group

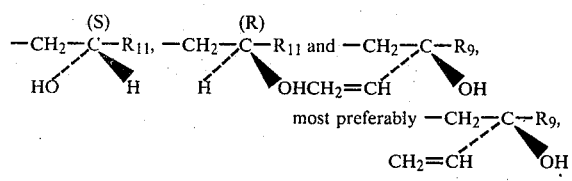

where R₉ and R₁₁ are as previously defined.

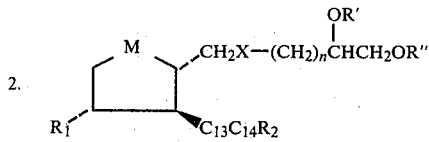

wherein R₂ is selected from the group

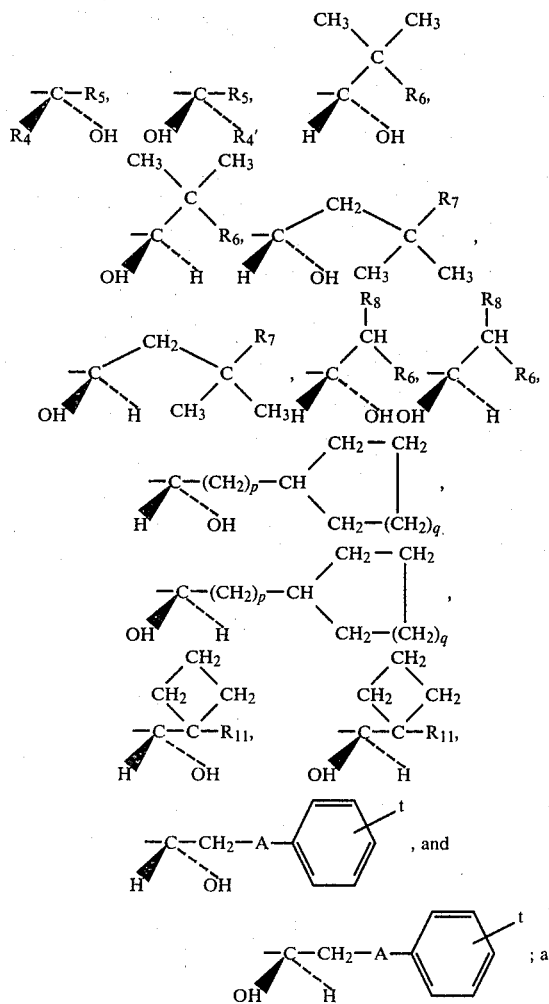

wherein M, X, R', R", R₁, R₄, R₅, R₆, R₇, R₈, R₁₁, n, p, q, t, A, and C₁₃-C₁₄ are as previously defined.

In the compounds of formula I(b), it is preferred that X is selected from the group —CH₂CH₂— and —CH=CH—(cis), most preferably —CH=CH—(cis); R' and R" are the same or different and are hydrogen or C₁ to C₄ alkanoyl, most preferably the same and are hydrogen, C₁₃-C₁₄ is —CH=CH—(trans) and R₂ is selected from the group

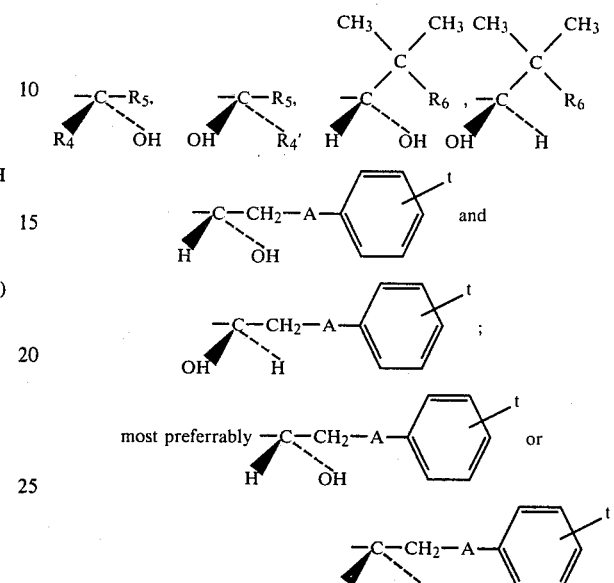

wherein n, M R₁, R₄, R₅, R₆, A and t are as previously defined.

The compounds of this invention can be prepared by a 1,4-conjugate-addition procedure involving treatment of an ether blocked cyclopentanone such as (74) or (80) with a lithio-cuprate reagent such as (84), (85), or (86), prepared as illustrated in Flowsheets A through L.

The 1,4-conjugate-addition procedure is described hereinbelow in Flowsheets L and M. The preparation of the various requisite 1-iodo-trans-1-alkenyl or 1-tributylstannyl-trans-1-alkenyl derivatives is illustrated in Flowsheets A-H and the methods of preparation of the 4-hydroxyclclopentenones embracing the 1-(hydroxymethyl)-1-hydroxy chain is described in connection with Flowsheets G and H.

FLOWSHEET A

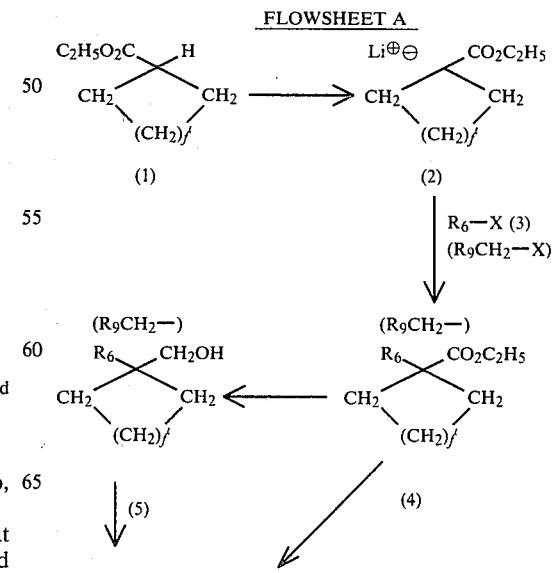

-continued
FLOWSHEET A

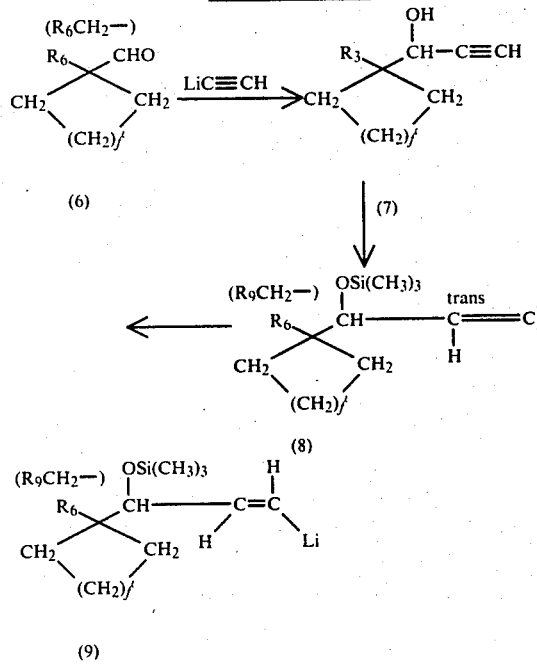

wherein f' is the integer one or two inclusive.

In accordance with the scheme as outlined hereinabove in Flowsheet A, carbethoxycyclobutane or carbethoxycyclopentane is converted to its enolate anion (2) by treatment with a strong base such as lithium cyclohexylisopropylamide, prepared from the corresponding amine and n-butyl lithium (hexane solution) in a solvent, such as anhydrous tetrahydrofuran, at very low temperatures, such as $-78°$ C. The resulting enolate anion (2) is then alkylated with $R_6$-X (3) to provide (4), the ester group of which is reduced to alcohol (5) by reaction with 2 equivalents of diisobutyl aluminum hydride, lithium aluminum hydride or the like. Oxidation of alcohol (5) with dipyridine chromium oxide complex ["Reagents for Organic Synthesis", L. F. Fieser and M. Fieser, John Wiley and Sons, Inc., New York, 4, 215 (1974)], prepared in situ in methylene chloride solution, provides the corresponding aldehyde (6), which can also be obtained directly from ester (4) by partial reduction with one equivalent of diisobutyl aluminum hydride at $-78°$ C., but the former two-step procedure is preferable. Reaction of aldehyde (6) with lithium acetylide-ethylenediamine complex provides the 3-hydroxy-1-alkyne (7), which is converted to its trimethysilyl ether in the usual manner. The silylated derivative is then treated with disiamylborane (prepared in situ in tetrahydrofuran solution at ice bath temperatures from 2-methyl-2-butene, sodium borohydride and boron trifluoride ethereate) then anhydrous trimethylamine oxide. The resulting solution and an iodine solution in tetrahydrofuran are then added simultaneously to an aqueous solution of sodium hydroxide to give the 1-iodo-3-trimethylsilyloxy-4,4-methylene-1-alkene (8). Also, the above sequence of reactions can be accomplished, as shown in Flowsheet A, using $R_9CH_2X$ where $R_9$ is a phenyl group.

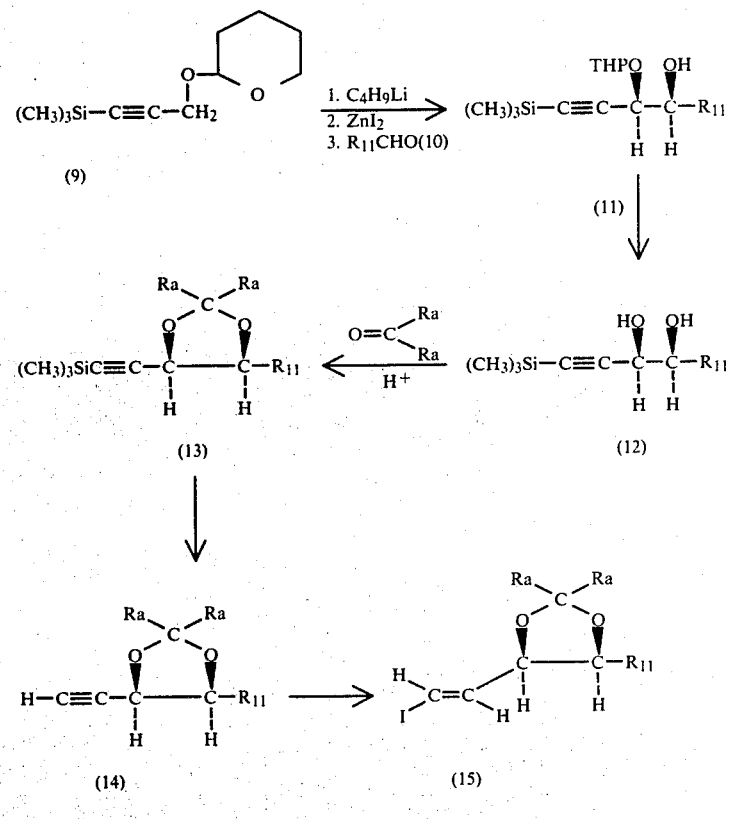

-continued
FLOWSHEET B
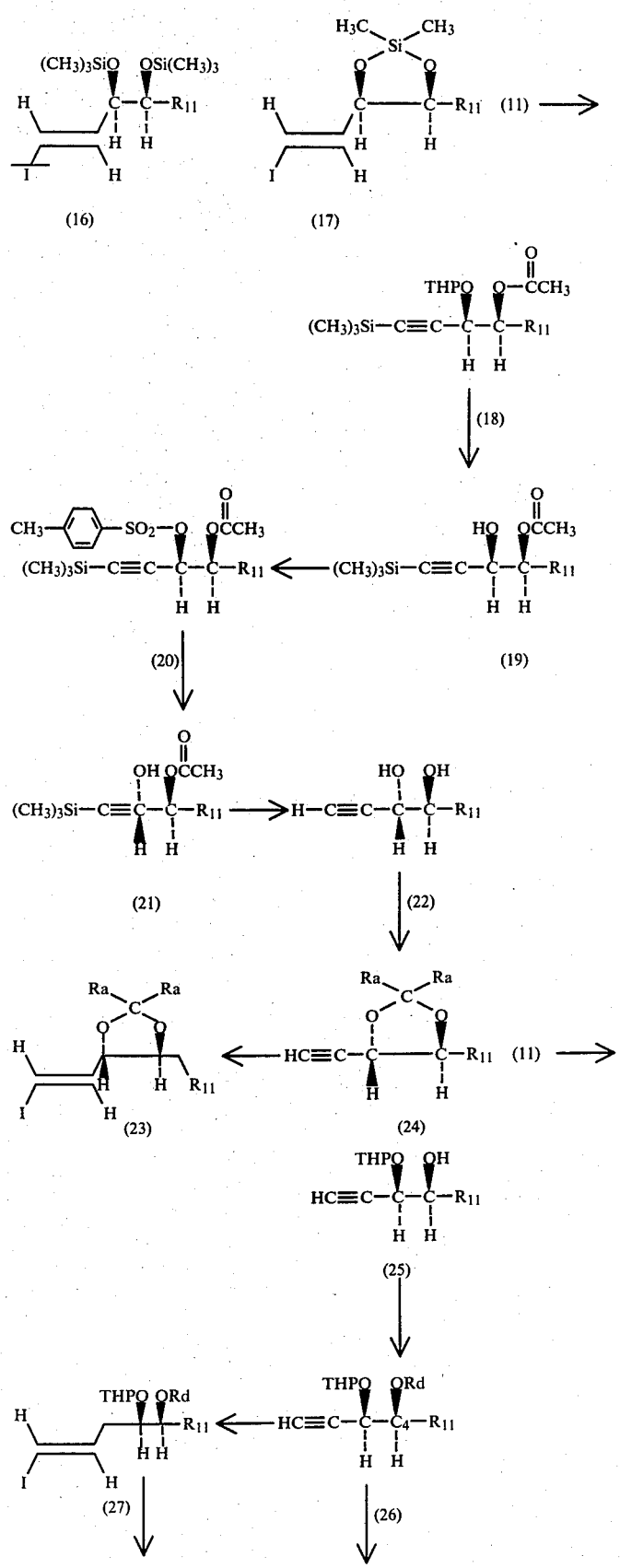

FLOWSHEET B
-continued

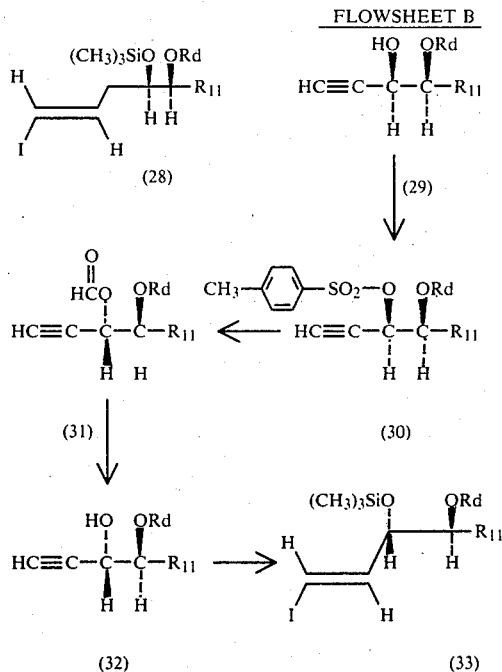

In accordance with the scheme as outlined hereinabove in Flowsheet B, 1-trimethylsilyl-3-tetrahydropyranyloxy-1-propyne (9) is treated with n-butyllithium at −78° C. and then with a freshly prepared solution of zinc iodide in anhydrous tetrahydrofuran, also at −78° C. Reaction of aldehyde (10) with the resulting reagent then provides the 4-hydroxy-3-tetrahydropyranyloxy-1-alkyne (11). This reaction is stereo specific, the product (11) being in the erythro configuration. (For additional information concerning this reaction see the examples which follow and F. Mercier, R. Epstein and S. Holland, Bull. Soc. Chim. France, 690(1972)).

The tetrahydropyranyl group in (11) is removed on weak acid treatment. The resulting erythro diol (12) can be reblocked by treating with an appropriate aldehyde or ketone

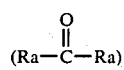

in the presence of strong acid catalyst in the usual way to give the ketal or acetal (13). Acetone is a useful ketone for this purpose and the product (13) is then a 3,4-isopropylidenedioxy-1-alkyne. It is also possible to utilize silyl blocking groups (introduced after removal of the 1-trimethylsilyl group) to ultimately give the vinyl iodides (16) or (17). Weak base treatment of (13), for example, heating for about one hour in refluxing methanol with potassium carbonate, results in desilylation to give (14). The 1-alkene (14) is converted to the corresponding 1-iodo-trans-1-alkene (15) by treatment with disamylborane (prepared in situ in tetrahydrofuran solution at ice bath temperatures from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give (15).

For the preparation of the threo derivatives, the 4-hydroxy-3-tetrahydropyranyloxy-1-alkyne (11) is acetylated to provide the corresponding 4-acetoxy derivative (18). The tetrahydropyranyl group is preferentially hydrolized with weak acid to (19), which is then tosylated in the usual manner to afford the erythro-3-tosyloxy-4-acetoxy-1-alkyne (20). Solvolysis of (20) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (21), which is then deblocked with aqueous base to give the threo-3,4-diol (22). Diol (22) is converted to an acetal or ketal (23) [or a silyl derivative as in (16) or (17)] and thence to the 1-iodo-trans-1-alkene (16) as described hereinabove wherein Ra is $C_1$ to $C_3$ alkyl.

For the preparation of the 16-alkoxyprostanoic acids of this invention, an erythro-4-hydroxy-3-tetrahydropyranyl-oxy-1-alkyne (11) is desilyated by a methanol-potassium carbonate treatment and the resulting (25) is alkylated to give the 4-alkoxy-3-tetrahydropyranyloxy-1-alkyne (26). A useful procedure for this step involves treatment of (25) with a molar equivalent of sodium hydride to give the 4-alkoxide which is then alkylated with the appropriate alkyl halide alkylating agent, for example methyl iodide. The 4-alkoxy-1-alkyne (26) is then converted to the corresponding 1-iodo-trans-1-alkene (27) as described hereinabove for the preparation of (15). If desired the tetrahydropyranyl blocking group in (27) can be hydrolyzed with weak acid and the resulting free 3-ol corresponding to (27) converted to the 3-trimethylsilyloxy derivative (28), in the usual manner, wherein $R_d$ is $C_1$ to $C_3$ alkyl.

For the threo series, the tetrahydropyranyl group in the erythro-4-alkoxy-1-alkyne (26) is cleaved and the resulting 3-hydroxy-4-alkoxy-1-alkyne (29) is tosylated to give the erythro-3-tosyloxy-4-alkoxy-1-alkyne (30). An $Sn_2$ displacement reaction of (30) with reagents such as tetrahydroammonium formate results in inversion to the threo derivative (31), saponification of which provides threo-3-hydroxy-4-alkoxy-1-alkyne (32). Trimethylsilylation followed by the vinyl iodide conversion procedure described hereinabove furnishes the threo-1-iodo-1-alkene (33) wherein Rd is hydrogen or $C_1$ to $C_3$ alkyl.

The 15-alkyl and/or 16-alkyl derivatives of this invention can be prepared by substituting

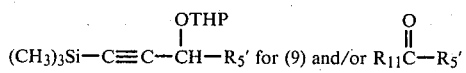

for (10) ($R_5'$=alkyl of 1 to 3 carbons) in Flowsheet B.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride ethereate) and then anhydrous trimethylamine oxide. The resulting solution and an iodine solution in tetrahydrofuran are added simultaneously to a sodium hydroxide solution to give the 1-iodo-4-trimethylsilyloxy-trans-1-alkene (36), precursors for 16-hydroxy-prostaglandins.

The trimethylsilyl protecting group is removed with mild acid and the resulting vinyl iodide alcohol is oxidized with pyridinium chlorochromate to provide the 1-iodo-4-oxo-trans-1-alkene (37), which upon treatment with a Grignard reagent ($R_{13}$MgX) provides the 1-iodo-4-hydroxy-trans-1-alkene, which is silylated in the usual manner to provide the silyl ether (38) wherein $R_{11}'$ is a $C_3$ to $C_7$ alkyl or alkenyl group and $R_{13}'$ is vinyl, cyclopropyl ethyl, or trimethylsilyethynyl.

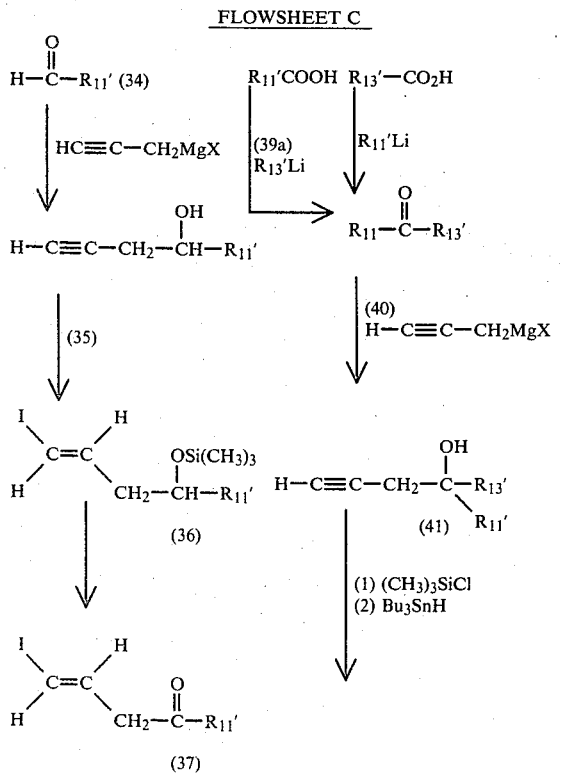

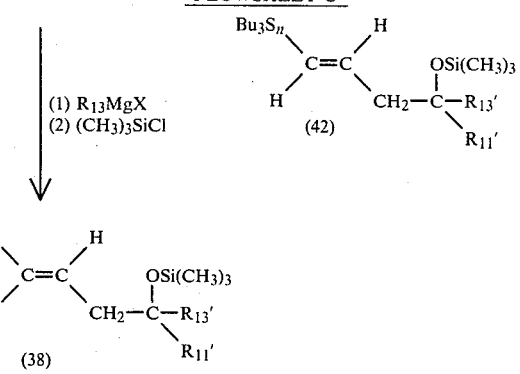

A preferred method for the preparation of vinyllithium precursor is also described in Flowsheet C. Treatment of the requisite carboxylic acid (39 or 39a) with the appropriate organolithium reagent ($R_{13}'$Li or $R_{11}'$Li respectively), wherein $R_{11}'$ and $R_{13}'$ are hereinabove defined, give the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of $-10°$ C. to $-78°$ C. generates the corresponding vinyllithium reagent.

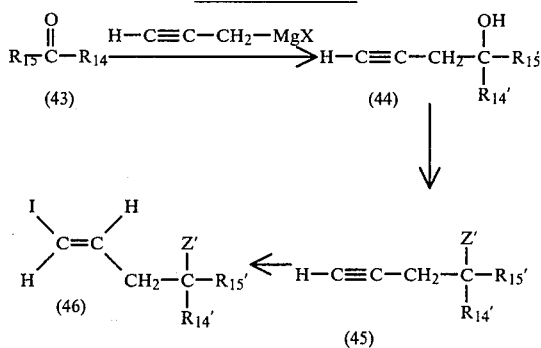

In accordance with Flowsheet D hereinabove, the precursors for other 16-hydroxy prostaglandins are prepared by treating an appropriate aldehyde or ketone (43) with a propargylic magnesium halide to yield the requisite homopropargylic alcohol (44). The alcohol is protected as a tritylether (45) (for secondary alcohols) or as a trimethylsilyl ether (45) (for tertiary alcohols). These ethers are then converted to the appropriate trans-vinyliodide (46) by treatment with disiamylborane generated in situ from 2-methyl-2-butene, sodium borohydride, and boron trifluoride, followed by treatment with trimethylamine oxide and then iodine and sodium hydroxide, wherein $R_{15}'$ is hydrogen, methyl or ethyl; $Z'$ is $-O-C(C_6H_5)_3$ when $R_{15}'$ is hydrogen and $Z'$ is $-O-Si(CH_3)_3$ when $R_{15}'$ is methyl or ethyl; $R_{14}'$ is selected from the group $C_3$ to $C_5$ alkyl, $C_3$ to $C_5$-1-alkenyl and

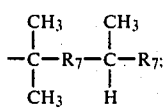

wherein $R_7$ is as described above with the proviso that when $R_{14}'$ is

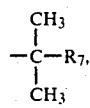

then $R_{15}'$ must be hydrogen.

hyde (50a) provides the respective vinylstannyl derivative (53a).

The preparation of the precursors for the synthesis of secondary 15-hydroxy congeners are described in the literature. The preparation of the precursor for 15-methyl-15-hydroxy is described in Flowsheet F hereinbelow. In accordance with Flowsheet F, an acid chloride, wherein $R_5$ is hereinabove defined, is treated with acetylene and aluminum trichloride to provide the vinylchloride (55) which upon treatment with sodium iodide furnishes the vinyliodide (56). Treatment of (56) with methylmagnesium halide followed by chlorotrimethylsilane gives the requisite protected vinyliodide (57).

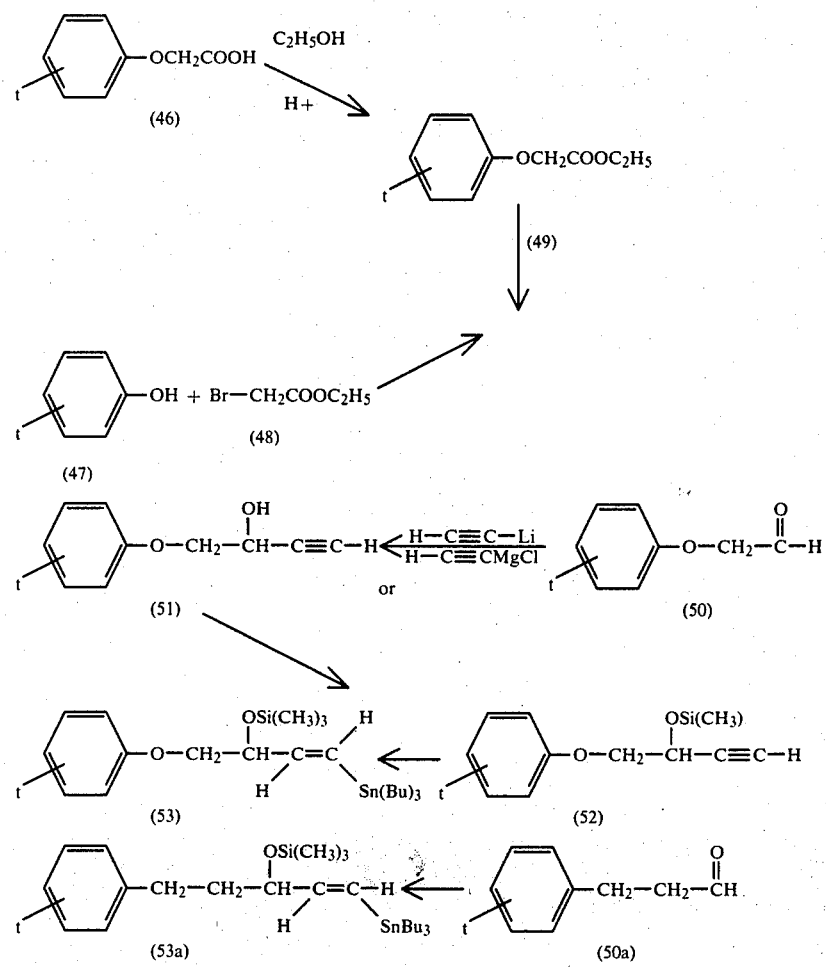

FLOWSHEET E

The preparation of the precursors for the synthesis of 16-aryloxy congeners is described in accordance with Flowsheet E hereinabove. The aryl esters (49) are prepared by esterifying the commercially available acids or by treatment of ethyl bromoacetate with the appropriate phenol. The ester (49) is reduced to the aldehyde (50) which upon treatment with lithium acetylide or acetylene magnesium bromide provides the propargylic alcohol (51). Treatment of the alcohol (51) with chlorotrimethylsilane followed by tri-n-butyltin hydride furnishes the requisite vinylstannyl derivative (53). Similar treatment starting with substituted hydrocinnamaldehyde

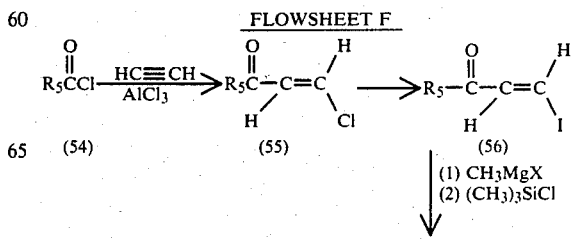

FLOWSHEET F

-continued
FLOWSHEET F

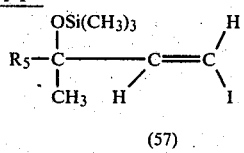

(57)

The procedures set forth above for the preparation of the various vinyl iodide and vinyl tin intermediates have been disclosed with particularity in the following U.S. Ser. No. 853,941, filed Oct. 22, 1979; U.S. Ser. No. 923,296, filed July 10, 1978 and U.S. Ser. No. 858,487, filed Dec. 8, 1977 incorporated herein by reference.

The preparation of the cyclopentenones useful in this invention containing the 1-hydroxy-1-hydroxymethyl feature (58 and 59) where $R_1$ is hydrogen or a hydroxy group can be accomplished in several ways.

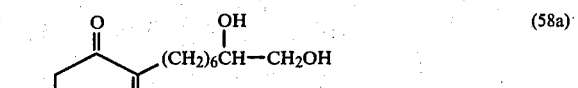

or

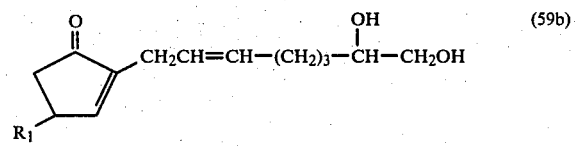

The preparation of the respective hydroxy-hydroxymethyl analogs and the protection of these compounds for a conjugate addition reaction is described hereinbelow in Flowsheets G and H.

For the preparation of cyclopentenones of the type wherein X is the group CH=CH—(cis), an alkyl vicinal diol-substituted triarylphosphonium halide is first prepared by reaction of 4-(ω-halo $C_4$ to $C_6$ alkyl)-2,2-dimethyl-1,3-dioxolane with triphenylphosphine in the presence of a polar inert solvent, for example dimethylformamide, acetonitrile, etc. sometimes admixed with acetone. (See Flowsheet G) The reaction is typically conducted at elevated temperatures (60°–100°) for from about 24 to 178 hours. The alkyldiol-substituted triphenylphoshonium halide (60) obtained is then used in a subsequent Wittig Reaction with a 2,5-dihydro-2,5-$C_1$ to $C_4$ alkoxy-2[3-(1-oxo)propyl]furan (61) to produce a 2,5-dihydro-2,5-di $C_1$ to $C_4$ alkoxy-2-(ω,ω-1-dihydroxy-3-$C_8$ to $C_{10}$ alkenyl) furan (62). The reaction is carried out in dimethylsulfoxide typically at 0° to 50° in the presence of the Wittig reagent, prepared from treating dimsyl sodium with compound (60) typically in the same inert solvent. Conversion of compound (62) to the required cyclopentenones (63) is effected by sequential treatment of (62) with wet silica gel and, after isolation of crude intermediate material, with aqueous mineral acid in a cosolvent such as dioxane or dimethoxyethane. A preferred system is one normal sulfuric acid in aqueous dioxane at reflux temperature for a period of 24 hours.

Protection of the hydroxy groups of compounds (63) suitable for the conjugate addition reaction is accomplished by treating these compounds with hexa $C_1$ to $C_4$ alkyl disilazane and a halotri $C_1$ to $C_4$ alkylsilane such as chlorotimethylsilane. The components are admixed in a suitable polar organic solvent, i.e., pyridine for from about 1 to 24 hours at 0° to 75° affording the compounds (64).

The preparation of cyclopentenones of the type used in the preparation of the compounds of formula I wherein X is —$CH_2CH_2$— is accomplished by reaction of a 2-hydroxy suberic, azelic or sebacic acid (65) acetone to yield the corresponding 4-(ω-carboxy $C_5$ to $C_7$ alkyl)-2,2-dimethyl-5-oxo-1,3-dioxolane (66). See Flowsheet H. The cyclization is carried out in the presence of catalytic amounts of an acid catalyst, i.e., sulfuric acid, hydrochloric acid, p-toluenesulfonic acid and the like, typically an inert organic solvent such as acetone, petroleum ether or mixtures thereof for a time and at a temperature sufficient to complete the reaction. Preferably the reaction is conducted under reflex conditions with the simultaneous azeotropic removal of water until no additional water accumulates in the distillate. Compounds (66) are converted, through the intermediacy of their mixed anhydrides with trifluoroacetic acid followed by Friedel-Crafts acylation of furan, into ω-(2-furoyl)-2-hydroxy $C_7$ to $C_9$ alkanoic acids (67). Typically the reaction is accomplished in a polar inert organic solvent, i.e., chloroform, methylene dichloride, etc., at 0° to 50° for 5 minutes to 40 hours. Compounds (67) are selectively reduced to compounds (68) using borane-tetrahydrofuran complex at temperatures of −10° to 20° over 1 to 24 hours. Solvents of preference include the linear and cyclic ethers such as diethyl ether, tetrahydrofuran, and the like.

Rearrangement of compounds (68) to the ω-(4-hydroxycyclopent-2-en-1-on-2-yl)alkane-1,2-diols, (69) is accomplished by: (1) Treatment of (68) with a solution of weak aqueous acid in a solvent such as dioxane or dimethoxyethane at a temperature of 75°–100°. A preferred system is two normal formic acid in aqueous dioxane at reflux temperatures for a period of 24 hours. (2) After completion of the first stage, the reaction solution is treated with a strong acid, preferably sulfuric acid in a quantity sufficient to make the solution one normal, and the resulting reaction solution is further heated to effect final conversion to (69). A preferred set of conditions employs the above-prepared solution one normal in sulfuric acid in aqueous dioxane at reflux temperatures for a period of 24 hours.

FLOWSHEET C

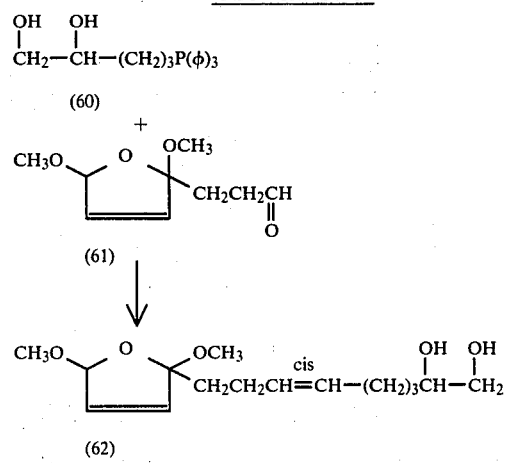

-continued
FLOWSHEET C

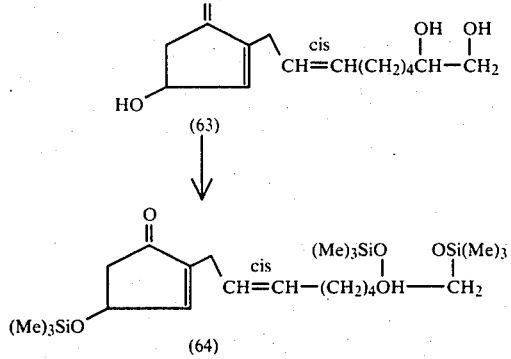

FLOWSHEET H

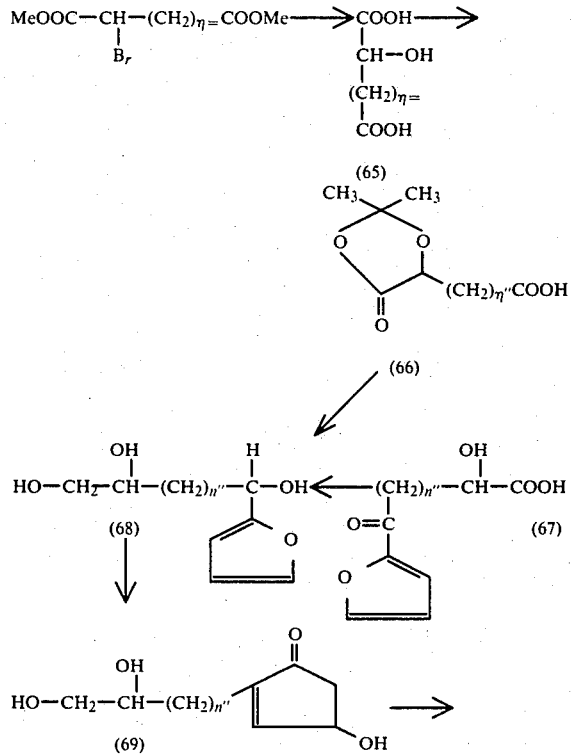

wherein n" = 5 to 7

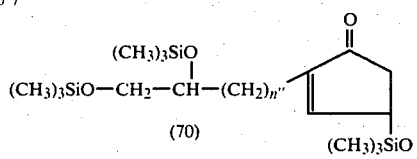

The hydroxy groups of compounds (69) may also be protected using the procedure described for compounds (63), which gives rise to compounds (70).

The preparation of the compounds of formula I from the requisite intermediate cyclopentenolones (the preparation of such of which being disclosed above) is accomplished by a conjugate addition reaction using organocopper reagents. These procedures are well known in the art and are described in, for example, C. J. Sih, et al J. Amer. Chem. Soc., 97 865 (1978). A brief description of the reaction sequence is set forth below and in the Preparation and Examples herein.

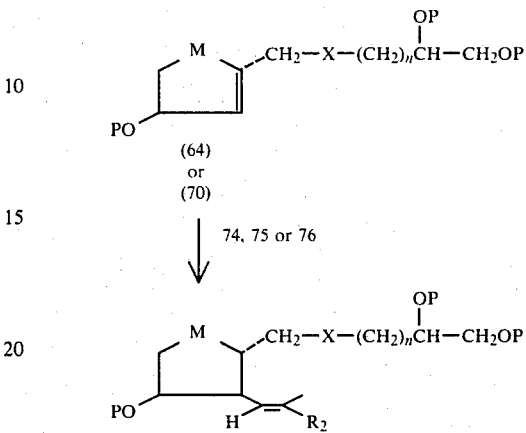

wherein P is a protecting group, M is C=O and $R_1$, $R_2$ and X are as previously defined. The protecting groups P are selected from any of the protecting groups well known to those skilled in this art and include the groups tri-$C_1$ to $C_4$ alkylsilyl, such as obtained from the silylchlorides; triphenylmethyl, such as obtained from the trityl halides; p-methoxy triphenylmethyl, from p-methoxytriphenylmethyl halides; methoxymethyl, from chloromethylmethylether; as well as those protecting groups obtained from 2-methoxypropane; dihydro-2H-pyran, ethylvinylithio and the like. Typically the hydroxy compounds of formula I are heated with an amount of the protecting group reagent, such in sufficient excess to assure complete reaction of each hydroxy moiety, i.e., 2 equivalents of protecting group reagent per equivalent of hydroxy moiety, in the absence or presence of an inert organic solvent.

In accordance with Flowsheet I a vinyliodide (71) is treatd with either one equivalent of n-butyllithium or 2 equivalents of t-butyllithium at low temperature, preferably $-30°$ to $-70°$ C. in an inert solvent, eg. hexane, either or toluene to provide the trans alkenyl-lithium reagent (73).

Alternatively, the vinyllithium reagent (73) can be prepared by treatment of a vinylstannyl derivative such as (72) with n-butyllithium at $-10°$ to $-78°$ in ether or THF.

For the preparation of the asymmetrical lithio cuprate (74) or the like, a solution of one molar equivalent of copper (I)-1-alkyne, preferably copper (I)-1-pentyne in anhydrous hexamethylphosphorus triamide preferably one to five molar equivalents, and anhydrous ether is added to one molar equivalent of the aforementioned vinyllithium solution cooled to about $-78°$ C. After about one hour at this temperature, a molar equivalent of the requisite cyclopentenone (64) or (70) is added. After several hours at $-78°$ C. to $-20°$ C. the reaction mixture is quenched with aqueous ammonium chloride solution and the blocked product (77) is isolated in the usual manner (and see Flowsheet J).

It is also possible to effect conjugate 1,4-addition with the asymmetrical lithio cuprate (76) derived from vinyllithium (73) and cuprous thiophenoxide. A solution of vinyllithium (73) in ether at −78° C. is reacted with an equimolar amount of a reagent prepared by admixture, in ether at a temperture of 0° C. to −78° C., of equimolar amounts of cuprous thiophenoxide and copper (I) iodide-tributylphosphonium complex. After about 30 minutes at this temperature, the lithio cuprate (76) is treated with the requisite cyclopentenone (74) or (70) as described hereinabove for the conjugate addition with 1-alkynyl lithio cuprate (74).

For the preparation of the symmetrical lithio cuprate (75) one molar equivalent of copper (I) iodide-tributylphosphine complex, dissolved in anhydrous ether, is added at about −78° C. to two molar equivalents of the aforementioned vinyl lithium (73) solution in hexane, cooled to −78° C. After about one hour at this temperature, the lithio cuprate (75) is treated with the requisite cyclopentane (64) or (70) as described hereinabove for the conjugate addition with the 1-alkynyl lithio cuprate (74). Removal of the blocking groups from (77) to give the prostaglandin congeners of formula I is accomplished by treatment of (77) with a mixture of acetic acid, tetrahydrofuran and water (4:2:1) at 25° C. to 55° C. Flowsheet J particularly illustrates these procedures where compounds (77)a, (77)b and (77)c are deblocked to yield the compounds of formula (I)a and (I)b.

FLOWSHEET I

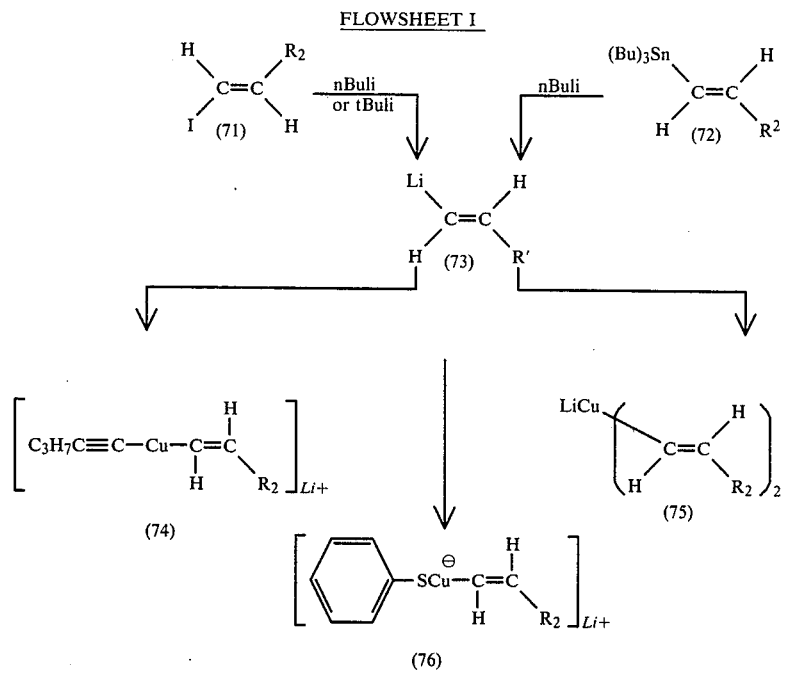

FLOWSHEET J

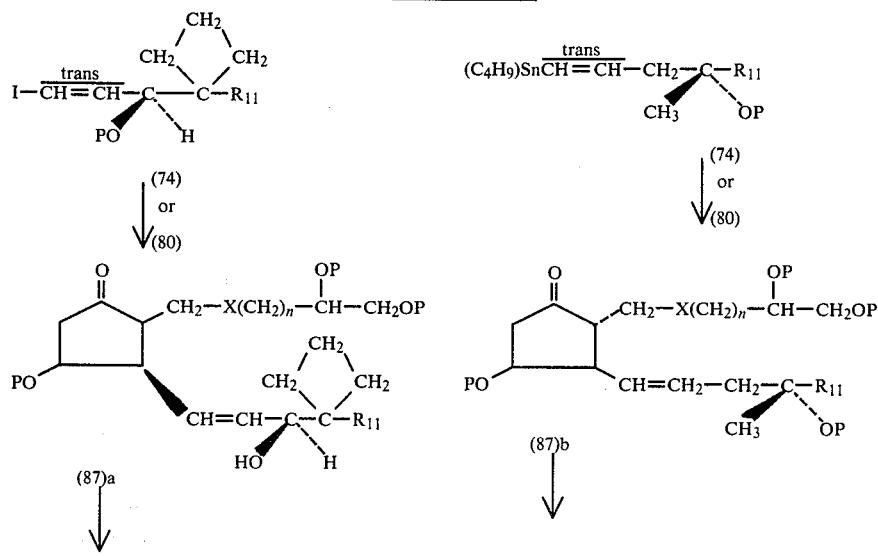

FLOWSHEET J -continued

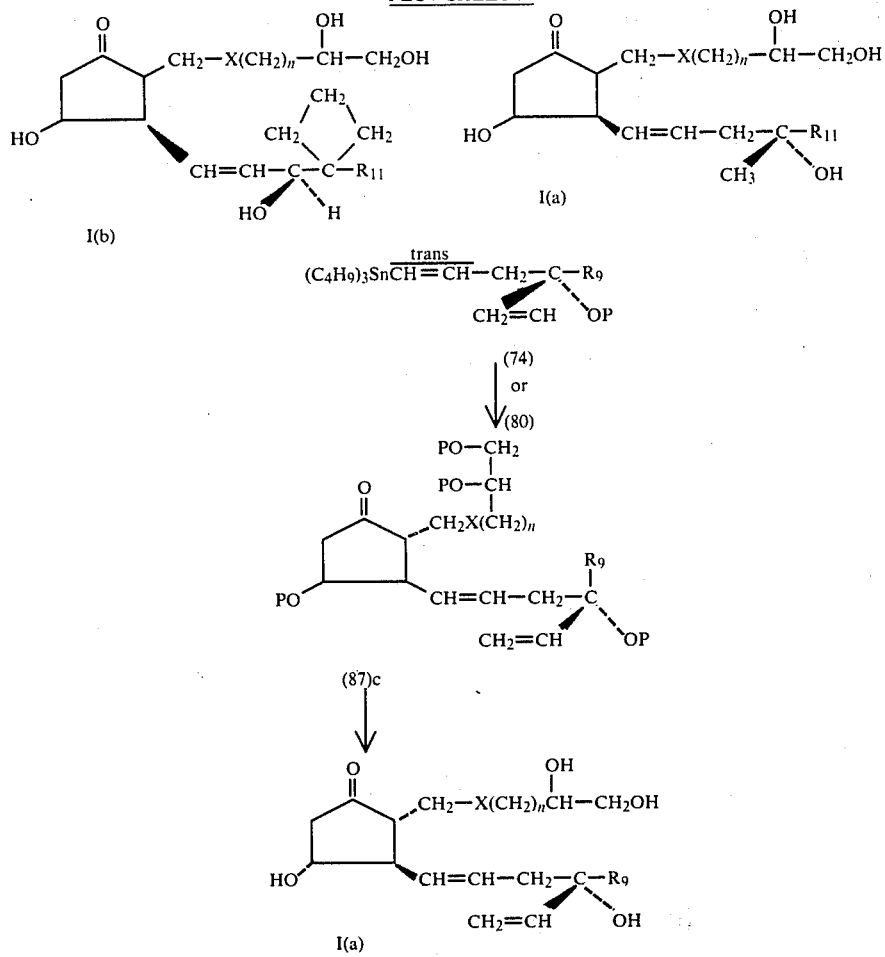

All available evidence indicates that the —CH=CH—R$_2$ function introduced by the cuprate process occupies a position trans to the 11-hydroxy function. Similarly, in the product (77) the two side-chains attached to C$_8$ and C$_{12}$ are trans to each other. However, the configurational relationship in the product as it is obtained directly from the cuprate process may be either cis or trans, i.e., these products may have the side-chains in a trans- or cis-relationship or they may be a mixture containing both the trans- and cis-isomers. This is indicated in the nomenclature of the compounds involved by the designation 8ξ. In order to ensure a trans-relationship in (77) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatograph including recycling techniques. [See G. Fallick, *American Laboratory*, 19–27 (August, 1973) as well as references cited therein. Additional information concerning high speed liquid chromatography and the instruments necessary for its application is available from Waters Associate, Inc., Maple Street, Milford, Mass.]

It is also possible to prepare the compounds of this invention in their optically active forms by the conversion of the optically active 2-(ω, ω-1 alkyldiol)-4-hydroxycyclopent-2-en-1ones (64) or (70) to the optically active protected analogs by procedure well known to the art. The compounds of formula I can be selectively esterified by dissolving the free hydroxy compounds in pyridine and adding one equivalent of an anhydride (R$_{15}$-CO)$_2$O or the acid chloride

and allowing the mixture to stand overnight to give the desired esters (78) and (79).

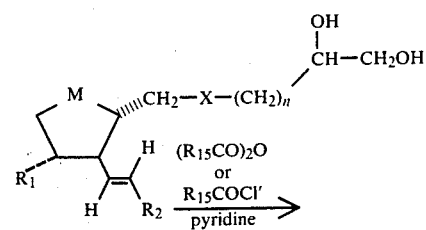

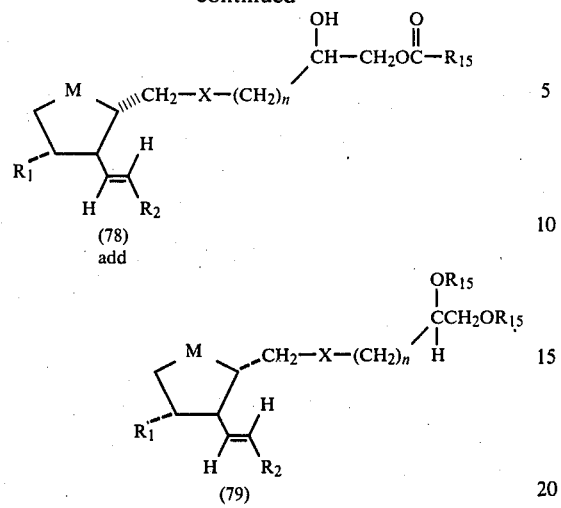

(78)
add

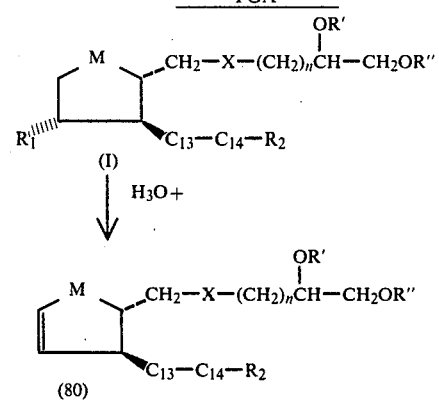

(79)

wherein $R_{15}$ is phenyl substituted with one or more groups such as alkyl ($C_1$-$C_4$), OR, SR, F, Cl, dialkylamino or $C_2$-$C_4$ alkyl, wherein M, $R_1$ and $R_2$ are as previously defined.

In accordance with Flowsheet K, where M=<C=O, when the 11-hdyroxy derivatives ($R_1$=hydroxy) or the 11-deoxy derivatives ($R_1$=H) are treated with dilute acid, or dilute base, it is possible to effect elimination and the formation of the corresponding derivative (80) prostaglandin of the A type. A preferred procedure involves treatment in tetrahydrofuran:water (2:1) solvent with 0.5 N in HCl for about 70 hours at ambient temperatures or alternativelly in methanol-water solvent (1:5) with 0.2 M potassium carbonate for 16 hours at ambient temperatures. Under acidic conditions, a tetrahydropyranyl or trialkysilyl ester will undergo hydrolysis.

The 9-keto derivatives of this invention can be converted to the corresponding 9-hydroxy derivatives as described in Flowsheet L. If this conversion is effected with sodium borohydride, the product is a mixture of 9α- and 9β-hydroxy derivatives (81) and (82) respectively, as set forth in the following reaction scheme, wherein $R_1$, $R_2$, and $C_{13}$-$C_{14}$ are as herein above defined.

When the reaction is carried out with lithium perhydro-9b-boraphenylyl hydride [H. C. Brown and W. C. Dickason, J. Amer. Chem. Soc., 92, 709, (1970)] or lithium tris-(t-butyl)-boronhydride [H. C. Brown and S. Krishnamurthy, ibid., 94, 7159 (1972)] the product is at least predominantly the 9α-hydroxy derivative wherein the 9-hydroxy group is cis to the side chain attached to $C_8$ and to the 11-hydroxy function, if present. In accordance with accepted convention, an α-substituent at the 8-, 9-, 11- or 12-positions is behind the plane of the paper, whereas a β-substituent at these positions is in front of the plane of paper. This is usually represented by a bond for an α-substituent, a ▬ bond for a β-substituent, and a ~ bond where both are indicated.

In accordance with Flowsheet M, wherein $R_2$ and $C_{13}$-$C_{14}$ are as described hereinabove, treatment of PGFα analogs with an oxidizing agent such as Jones reagent or pyridinium chlorochromate provides a selective oxidation of the 11α-hydroxly to provide compounds of the PGD structure such as (82a).

FLOWSHEET K
PGA

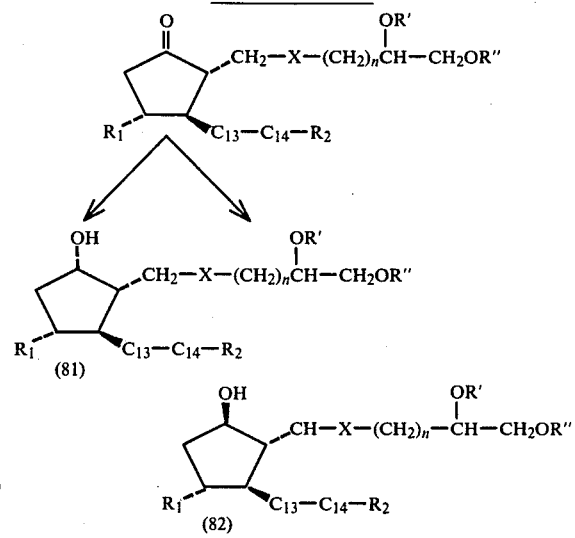

FLOWSHEET M

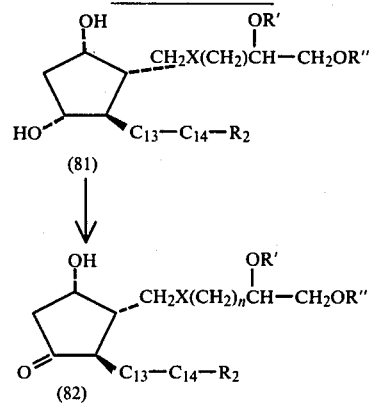

When the compounds of this invention are prepared from racemic starting compounds, a mixture of racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information concerning high speed liquid chromatography and the instruments necessary for its application is available from Waters Associate Inc., Maple Street, Milford, Mass.]

The 4-hydroxycyclopenteneone racemates may be resolved into their component enantiomers (83) and (84) wherein n, X, R' and R" are as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride (to give (85)), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (83) and (84). A useful procedure for the resolution of a 4-hydroxycyclopentenone racemate via an oxime such as (95) is described in the art [R. Pappo, P. Collins and C. Jung, *Tetrahedron Letters*, 943 (1973)]. The resolution of the hydroxycyclopentenone (83) wherein —CH$_2$—X(CH$_2$)$_n$— is

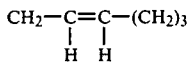

is described by Bruhn et al, *Tetrahedron Letters*, 235 (1976).

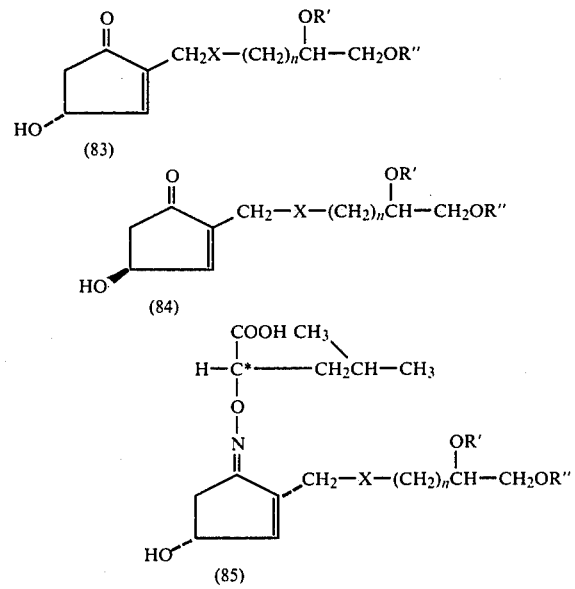

Other useful ketone derivatizing agents are optically active 1,2-glycols, e.g., D(-)-2,3-butanediol, or 1,2-dithiols, e.g., L(+)-2,3-butanedithiol. These are used to convert the 9-oxo derivative to 9,9-alkylenedioxa or 9,9-alkylenedithia derivatives, separation of diastereomers by chromatographic procedures followed by regeneration of the individual 9-oxo diastereomer by ketal cleavage all by procedures well-known in the art. Both ketalization and deketalization would have to be accomplishded by procedures which would not disrupt the 11-oxo-9-keto system, which of course, is not a problem in the 11-unsubstituted series.

An alternate procedure for the preparation of the 4(R)-hydroxycyclopentenone enantiomers such as (93) involves as a key step the selective microbiological or chemical reduction of trione (86) to the 4(R)-hydroxycyclopentanedione (87). A wide variety of microorganisms are capable of accomplishing this asymmetric reduction, one of the most useful being *Dipodascus unincleatus*. This step also can be achieved chemically be catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine) rhodium (I) tetrafluoroborate in the presence of one equivalent of organic base, such as triethylamine.

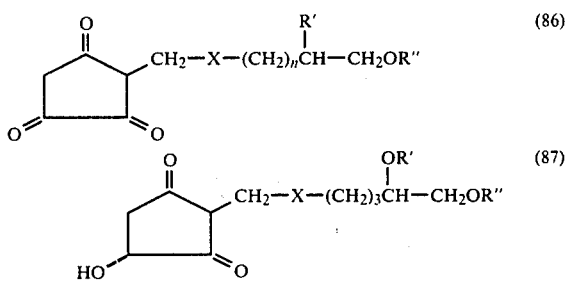

Procedures for the preparation of the requisite cyclopentanetriones are well-established in the art and generally involve the treatment of an ω-1-oxo long chain ester with methyl or ethyl oxalate and a base such as sodium methoxide in methanol, followed by treatment with hydrochloric acid in aqueous methanol. See J. Kutsube and M. Matsui, *Agr. Biol. Chem.*, 33 1078 (1969); P. Collins, C. J. Jung and R. Pappo, *Israel Journal of Chemistry* 6, 839 (1968); R. Pappo, P. Collins and C. Jung, *Ann. N. Y. Acad. Sci.*, 180, 64 (1971); C. J. Sih, et al., *J. A. C. S.*, 95, 1676 (1973) (see reference 7); and J. B. Heather, et al., *Tetrahedron Letters*, 2313 (1973) for pertinent background literature.

It is also possible to resolve the 4-hydroxycyclopentenone racemate (88) by microbiological means. Thus, treatment of the 4-O-alkanoyl or aroyl derivatives ((89), $R_{18}$=aryl or alkyl) of racemate (88) (preferably the 4-O-acetyl and 4-O-propionyl derivatives) with an appropriate microorganism, preferably a Saccharomyces species e.g., 1375-143, affords preferential de-O-acrylation of the 4(R)-enantiomer to give (190), which is then separated from the unreacted 4(S)-O-acyl enantiomer (191) by chromatographic procedures. After separation, mild hydrolysis yields the 4(S) hydroxycyclopentenone (192). [See N. J. Marsheck and M. Miyano, *Biochima et Biphysica Act*, 316, 363 (1973) for related examples.]

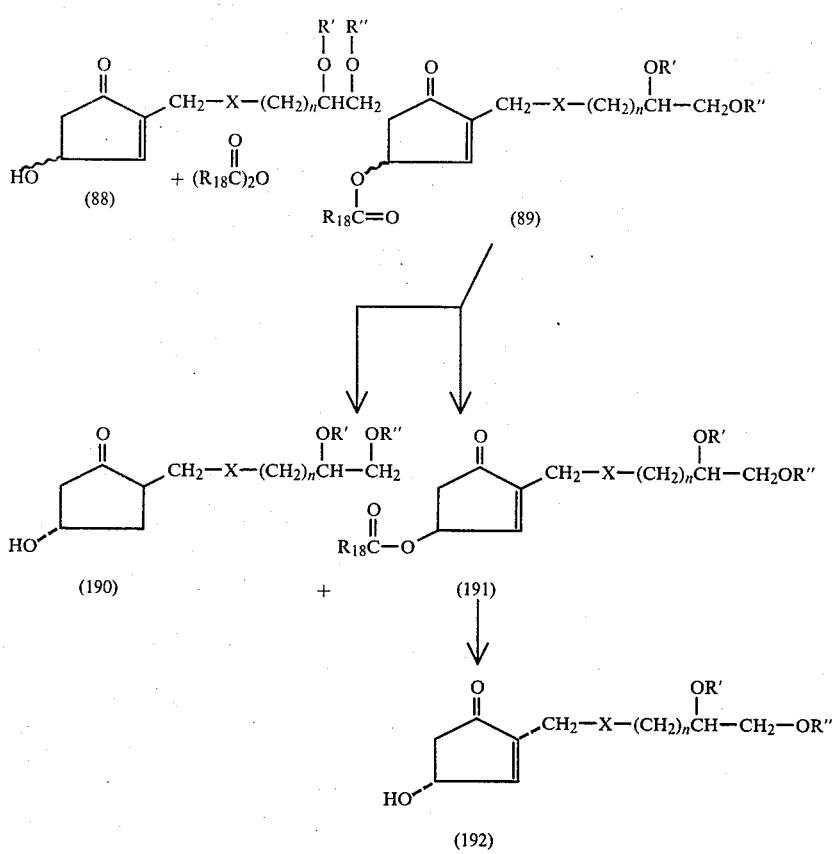

It is also possible to prepare the individual 4-hydroxycyclopentenones (190) and (192) directly by selective microbial hydroxylations of the corresponding 4-unsubstituted cyclopentenone (193). For example, with *Aspergillus niger* ATCC 9142; a selective 4(R)-hydroxylation of [(148, Z=(CH$_2$)$_6$] has been reported; see S. Kurozumi, T. Tora and S. Ishimoto, Tetrahedron Letters 4959 (1973). Other microorganisms can also accomplish this hydroxylation.

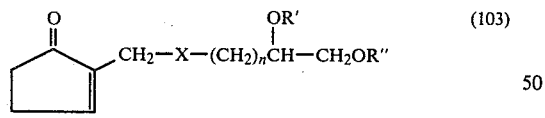

The novel compounds of the present invention have potential utility as hypotensive agents, anti-ucler agents, agents for the treatment of gastric hypersecretion and gastric erosion, agents to provide protection against the ulcerogenic and other gastric difficulties associated with the use of various non-steroidal antiinflammatory agents (e.g., indomethacin, aspirin, and phenylbutazone), bronchodilators, antiinflammatory agents, abortifacients, agents for the induction of labor, agents for the induction of menses, fertility-controlling agents oestrus regulators for the use in animal husbandry with cattle and other domestic animals and central nervous system regulatory agents. Certain of the novel compounds of this invention possess utility as intermediates for the preparation of other of the novel compounds of this invention.

The ring system of certain of the novel compounds. of this invention allow them to be characterized as follows:

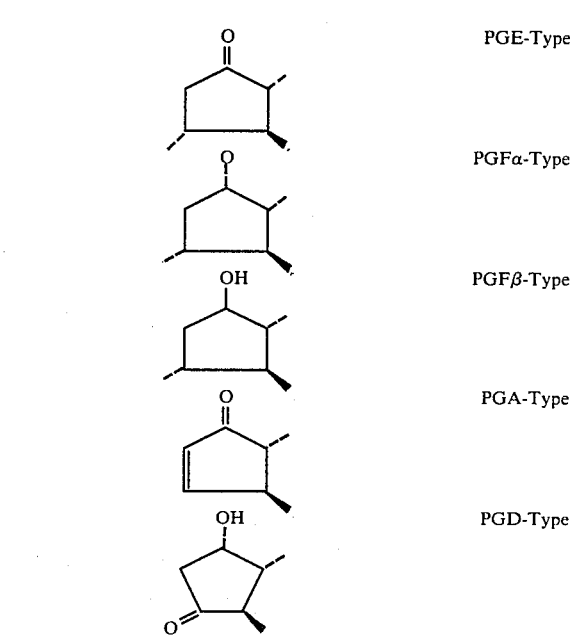

The novel compounds of this invention posses the pharmacological activity described below as associated with the appropriate above-described prostaglandin type.

The known PGE, PGF$_\alpha$, PGF$_\beta$, PGA and PGD compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGF$_\alpha$ and PGF$_\beta$ compounds are additionally selective in that they are at most relatively very weak stimulants of smooth muscle. The 11-deoxy PGE compounds have a further advantage in that they are much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$ and dihydro-PGE$_1$, and the corresponding PGF$_\alpha$, PGF$_\beta$, and PGA, compounds, and their esters and pharmacologically acceptable salts, are extremely potent in causing various biological responses. For that reason, these compounds are useful for pharmacological purposes. See, for example, Bergstron, et al., *Pharmacol. Rev.*, 20, 1 (1968), and references cited therein. A few of those biological responses are systemic arterial blood pressure lowering in the case of the PGE, PGF$_\beta$, and PGA compounds as measured, for example, in anesthetized (phenobarbital sodium) pentolinium-treated rats with indwelling aortic and right heart cannulas; pressor activity, similarly measured, for the PGF$_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g to about 10 mg per ml of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 g to about 500 $\mu$g per kg of body weight per minute, or in a total daily dose by injection or infusion in the range of about 0.1 mg to about 20 mg per kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE$_1$ and PGD$_2$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 mg to about 20 mg per kg of body weight per day are used, the exact dose depending on the age, weight, and condition of the patient or animal, and on the frequency and route of administration.

11$\alpha$-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore PGE$_2$, for example, is useful in place of or in combination with less than usual amounts of these known smooth muscle stimulators, for example to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 µg to about 50 µg per kg of body weight per minute until the desired effect is obtained. Subsequent doses are given by intravenous, subcutaneous, or intramuscular injection or infusion during puerperium in the range of 0.01 mg to 2 mg per kg of body weight per day, the exact dose depending on the age, weight, and condition of the patient or animal.

The PGE, PGF$_\beta$ and PGA compounds are useful as hypotensive agents to reduce blood pressure in mammals including man. For this purpose, the compounds are administered by intra venous infusion at the rate about 0.01 µg to about 50 µg per kg of body weight per minute, or in a single or multiple doses of about 25 µg to 2500 µg per kg of body weight total per day.

The PGE, PGF$_\alpha$, and PGF$_\beta$ compounds are useful in place of oxytocin to induce labor in pregnant female animals, including man, cows, sheep, pigs, at or near term or in pregnant animals with intrauterine death of the fetus from about 20 weeks to term. For this purpose, the compound is infused intravenously at a dose 0.01 µg to 50 µg per kg of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started.

The PGE, PGF$\alpha$, and PGF$_\beta$ compounds are useful for controlling the reproductive cycle in ovulating female mammals, including humans and other animals. For that purpose, PGF$_2\alpha$, for example, is administered systemically at a dose level in the range of 0.01 mg to about 20 mg per kg of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly, they are useful as abortifacients. They are also useful for induction of menses during approximately the first two weeks of a missed menstrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrom and early kidney transplant rejection. In case of excessive or inappropriate ADH antidiuretic hormone vasopressin secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 2 to 2000 µg/ml of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluoroprednisoline, each of those being used in combination at the usual concentrations suitable for its use alone.

The novel compounds of this invention induce the biological responses described hereinabove as associated with its particular prostaglandin type. These novel compounds are accordingly used for the above-described corresponding purposes.

The novel PGE, PGF$_\beta$ and PGA compounds of this invention are also useful as bronchodialtors for the treatment of asthma and chronic bronchitis. As such they may be conveniently administered by inhalation of aerosol sprays prepared in a dose range of about 10 µg to about 10 mg/ml of a pharmacologically suitable liquid vehicle. Relative to the natural prostaglandins, the PGE compounds in particular have the significant advantage of inducing prolonged effects.

The compounds of this invention are useful as vasodilators whose activity may be restricted to the site of application by control of the dose applied. Compositions containing the compounds of this invention may be applied topically and by local injection to increase peripheral circulation or to treat peripheral vascular disorders of the arteriospastic and occlussive types. Compositions for topical administration containing prostaglandins similar to those of this invention are disclosed by application Ser. No. 934,199 filed Aug. 16, 1978 and application Ser. No. 011,364 filed Feb. 12, 1979. The compounds of this invention may be employed as vasodilators for topical application in the compositions and dosages described by the above-cited applications. Typically topical preparations contain from about 0.3 to 20% by W/W of the compounds of this invention in a pharmaceutical carrier, and preferably from about 1% to 5% by W/W of the prostaglandin.

The compounds of this invention may also be administered topically or by local injection to lower the systemic blood pressure of man and warm blooded animals. Systemic action is obtained by the use of an effective dosage greater than that used to induce localized action at the site of application. The effective dosage of the compounds of this invention administered topically in a pharmaceutical carrier for systemic effect is about 0.1 mg. to 10 mg per kg. of body weight per day. Pharmaceutical carriers and compositions which may be employed are disclosed by application Ser. No. 934,199, filed Aug. 16, 1978.

This invention will be described in greater detail with reference to the following preparations and examples.

PREPARATION 1

2-Hydroxynonanedioic Acid

A stirred mixture of 295 g. of dimethyl 2-bromononanedioate, [*Acta. Chim. Acad. Sci. Hung.*, 46, 85 (1965)], 371 g. of anhydrous sodium carbonate, and 3 liters of water is heated at reflux for 22 hours. The solution which forms is cooled and acidified with 600 ml. of 12N hydrochloric acid. The mixture is saturated with sodium chloride and extracted with ethyl acetate. The extract is washed with brine, dried over magnesium sulfate, and concentrated to give 184 g. of white solid, m.p. 86°–92° C.

PREPARATION 2

4-(6-Carboxyhexyl)-2,2-dimethyl-5-oxo-1,3-dioxolane

A stirred mixture of 10.2 g. of 2-hydroxynonanedioic acid, 50 ml. of acetone, 75 ml. of petroleum ether (b.p. 30°–55° C.), and 0.25 ml. of sulfuric acid is heated at reflux for 7 hours with azeotropic removal of water. The stirred mixture is treated with 0.59 g. of sodium carbonate and diluted with petroleum ether. The solution is decanted from solid and concentrated to give 9.4 g. of oil; pmr (CDCl$_3$) δ1.58 and 1.63 (gem-dimethyl group).

PREPARATION 3

To a stirred, ice-cold solution of 83 g. of 4-(6-carboxyhexyl)-2,2-dimethyl-5-oxo-1,3-dioxolane in 340 ml. of dichloromethane is added 48 ml. of trifluoroacetic anhydride during 5 minutes. The solution is warmed to 20° C. during 10 minutes, recooled to 0° C., and then is treated with 122 ml. of furan during 10 minutes. The resulting solution is stirred at room temperature for 16 hours. The solution is treated with water after which the organic layer is dried over magnesium sulfate and concentrated.

A solution of the resulting oil in 340 ml. of acetone is treated with 340 ml. of 1.0 N hydrochloric acid. After 4 hours the solution is concentrated and then extracted with ethyl acetate. The extract is washed with brine, dried over magnesium sulfate, and concentrated to give an oil; pmr (CDCl$_3$) δ 2.83 (triplet) and 4.27 (multiplet).

PREPARATION 4

9-(2-Furyl)-1,2,9-nonanetriol

To 640 ml. of 1.0 M. boranetetrahydrofuran complex in tetrahydrofuran is added a solution of 81 g. of 8-(2-furoyl)-2-hydroxyoctanoic acid in 240 ml. of tetrahydrofuran during one hour while maintaining a temperature of 0°–10° C. After the addition, the solution is stirred at room temperature for 3 hours, is cooled to 0° C., and treated cautiously with 80 ml. of 1:1 aqueous tetrahydrofuran. The resulting mixture is diluted with ethyl acetate. The solution is washed successively with an ice-cold brine-hydrochloric acid mixture, brine, brine-sodium bicarbonate solution and brine. The solution is dried over magnesium sulfate and concentrated to give an oil; pmr (CDCl$_3$) δ 4.70 (triplet).

PREPARATION 5

8-(4-Hydroxycyclopent-2-en-1-on-2-yl)-1,2-octanediol

To a stirred mixture of 71 g. of 9-(2-furyl)-1,2,9-nonanetriol, 0.30 g. of hydroquinone, 18.5 g. of sodium bicarbonate, 1320 ml. of dioxane, and 990 ml. of water is added cautiously, 197 ml. of 90% formic acid. The resulting solution is heated at reflux temperature for 20 hours.

The stirred solution is cooled, treated dropwise with 68 ml. of concentrated sulfuric acid during 15 minutes, and then is heated at reflux temperature for 18 hours. The solution is cooled, saturated with sodium chloride, and extracted with ethyl acetate. The extract is washed with brine, dried over magnesium sulfate, and concentrated. The resulting crude product is purified by chromatography on silica gel with ether progressively enriched in methanol to give an oil; pmr (CDCl$_3$) δ 5.94 (multiplet) and 7.22 (broad singlet).

PREPARATION 6

2-(7′,8′-Bistrimethylsilyloxyoctyl)-4-trimethylsilyloxycyclopent-2-en-1-one

To a stirred, ice-cold solution of 8.2 g. of 8-(4-hydroxycyclopent-2-en-1-on-2-yl)-1,2-octanediol in 100 ml. of pyridine is added 26 ml. of hexamethyldisilazane followed by 13 ml. of chlorotrimethylsilane. The resulting mixture is stirred at room temperature for 4 hours. Solvent and excess reagents are removed by evaporation under vacuum, and the residue is treated with petroleum ether and filtered through celite. The residue obtained after solvent evaporation of the filtrate is subjected to Kugelrohr distillation at 160° C. to provide a colorless liquid.

PREPARATION 7

2,2-Dimethyl-4-(4-p-toluenesulfonyloxybutyl)-1,3-dioxolane

To a stirred, ice-cold solution of 6.97 g. of 2,2-dimethyl-4-(4-hydroxybutyl)-1,3-dioxolane [*Chem. Abstr.*, 67, 32617f (1967)] in 40 ml. of pyridine is added 9.2 g. of p-toluenesulfonyl chloride. The mixture is kept at 0°–5° C. overnight, diluted with ice water, and extracted with ether. The extract is washed successively with water, sodium bicarbonate, water, and brine. The extract is dried over magnesium sulfate and concentrated to give a syrup; pmr (CDCl$_3$) δ 2.50 (singlet).

PREPARATION 8

4-(4-Bromobutyl)-2,2-dimethyl-1,3-dioxolane

To a stirred solution of 220 g. of 2,2-dimethyl-4-(4-p-toluenesulfonyloxybutyl)-1,3-dioxolane in 800 ml. of dimethylformamide at 0° C. is added 115 g. of anhydrous lithium bromide in portions during 5 minutes. The resulting mixture is stirred at ambient temperature for 22 hours, diluted with water, and extracted with ether. The extract is washed with sodium bicarbonate solution, water, and brine; dried over magnesium sulfate; and concentrated. The residue is distilled to give a colorless liquid, b.p. 71°–74° C. (0.2 mm.).

PREPARATION 9

(5,6-Dihydroxyhexyl)triphenylphosphonium bromide

A stirred solution of 125 g. of 4-(4-bromobutyl)-2,2-dimethyl-1,3-dioxolane, 154 g. of triphenylphosphine, 800 ml. of acetonitrile, and 270 ml. of acetone is heated at reflux for 69 hours. The solvents are removed under vacuum, and the residue is treated with 250 ml. of chloroform and 15 ml. of water. The resulting mixture is stirred vigorously for 30 minutes. The solvents are removed with the aid of benzene chaser, and the solid product is washed with ether and dried under vacuum to give white crystals, m.p. 152°–170° C.

PREPARATION 10

2,5-Dihydro-2,5-dimethoxy-2-(8',9'-dihydroxy-3'-cis-octenyl)furan p A solution of 37.2 g. of 2,5-dihydro-2,5-dimethoxy-2-(3'-oxopropyl)furan in 150 ml. of dimethylsulfoxide is added during 20 minutes at 18°–20° C. to the Wittig reagent prepared from 200 ml. of 1 M. dimsyl sodium in dimethylsulfoxide and 96 g. of (5,6-dihydroxyhexyl)triphenylphosphonium bromide in 300 ml. of dimethylsulfoxide. The resulting solution is stirred at 25° C. for 17 hours. The solvent is removed under vacuum, and the residue is treated with brine and extracted with ethyl acetate. The extract is washed with water and brine, dried over magnesium sulfate, and concentrated to give an oil, pmr (CDCl$_3$) $\delta$ 5.5 (multiplet).

PREPARATION 11

2-(7',8'-Dihydroxy-2'-cis-octenyl)-4-hydroxycyclopent-2-en-1-one

To a well-agitated and cooled solution of 100 g. of crude 2,5-dihydro-2,5-dimethoxy-2-(8',9'-dihydroxy-3'-cis-octenyl)furan in 1500 ml. of chloroform is added 2400 g. of silica gel and 250 ml. of water. After evaporation of 750 ml. of chloroform the resulting slurry is kept at 25° C. for 6 days, and then eluted with 8 liters of 4:1 ethyl acetate-methanol.

The eluate is concentrated, and the residue is dissolved in 900 ml. of dioxane and 600 ml. of water. To the stirred solution is added 100 mg. of hydroquinone and 42 ml. of sulfuric acid dropwise during 10 minutes. The resulting solution is heated under reflux for 21 hours, cooled, saturated with sodium chloride, and extracted with ethyl acetate. The extract is washed with brine, dried over magnesium sulfate, and concentrated. The residue is subjected to column chromatography on silica gel with ether progressively enriched in methanol to give an oil; pmr $\delta$ 5.97 (multiplet) and 7.22 (broad singlet).

PREPARATION 12

2-(7',8'-Bistrimethylsilyloxy)-2'-cis-octenyl)-4-trimethylsilyloxycyclopent-2-en-1-one To a stirred, ice-cold solution of 4.8 g. of 2-(7',8'-dihydroxy-2'-cis-octenyl)-4-hydroxycyclopent-2-en-1-one in 60 ml. of pyridine is added successively 15 ml. of hexamethyldisilazane and 7.6 ml. of chlorotrimethylsilane. The resulting mixture is stirred at ambient temperature for 5 hours. The excess reagents and solvent are removed under vacuum, and the residue is slurried with petroleum ether and filtered through Celite. The filtrate is concentrated to give an amber liquid.

The following examples are illustrated of the various E$_1$ and E$_2$-series prostaglandins all bearing the 1-hydroxy-1-hydroxymethyl moiety. The preparative procedure is exemplified in detail in the previous examples, Examples 1–5. The compounds of these examples, Examples 6–179 i.e., the vinyl iodides or vinyl stannanes and the coreactant cyclopentenones, on substitutions for the corresponding compounds in the earlier examples affords the identified prostaglandin compound.

EXAMPLE 1

11$\alpha$,16-Dihydroxy-1-hydroxymethyl-16-methyl-,9-oxo-13-trans-prosten-1-ol

A stirred solution of 5.04 g. of 1-tri-n-butylstannyl-4-methyl-4-trimethylsiloxy-1-trans-octen in 8.0 ml. of tetrahydrofuran is treated with 4.0 ml. of 2.0 M. n-butyllithium in hexane at −78° C. The resulting solution is stirred at −40° C. for 2 hours, recooled to −78° C., and treated with a solution prepared from 1.16 g. of copper pentyne, 3.2 ml. of hexamethylphosphorous triamide, and 20 ml. of ether. The resulting solution is stirred at −78° C. for one hour and then treated with a solution of 1.84 g. of 2-(7',8'-bistrimethylsilyloxyoctyl)-4-trimethylsilyloxycyclopent-2-en-1-one (Preparation 6) in 10 ml. of ether during 5 minutes. The resulting solution is stirred at −40° C. for 90 minutes, recooled to −78° C., and quenched with a solution of 1.0 ml. of acetic acid in 20 ml. of ether.

The mixture is diluted to 150 ml. with ether and poured into a stirred, ice-cold mixture of 40 ml. of saturated ammonium chloride solution and 40 ml. of 1.0 N hydrochloric acid. The ether layer is washed successively with 2.0 N hydrochloric acid, water, and brine; dried over magnesium sulfate; and concentrated.

The residue is treated with a solution prepared from 32 ml. of acetic acid, 16 ml. of tetrahydrofuran, and 8 ml. of water, and the resulting mixture is stirred at 40° C. for 60 minutes. The mixture is cooled and partitioned with ethyl acetate and half-saturated brine. The organic layer is washed with brine, dried over magnesium sulfate, and concentrated to give a mixture of oil and liquid tetrabutylstannane. These materials are separated by successive elution through silica gel with hexane and ethyl acetate. The ethyl acetate eluate is concentrated, and the residue is subjected to chromatography on silica gel to provide an oil.

EXAMPLE 2

11$\alpha$,16-Dihydroxy-1-hydroxymethyl-16-methyl-9-oxo-5-cis-13-trans-prostadien-1-ol A stirred solution of 2.52 g. of (4-methyl-4-trimethylsiloxy-1-trans-octenyl)tributylstannane in 5.0 ml. of tetrahydrofuran is treated with 2.1 ml. of 2.4 M. n-butyllithium in hexane at −78° C. The solution is stirred at −40° C. for 1.5 hours, warmed to −30° C. during 15 minutes, and recooled to −78° C. The stirred solution is treated with a solution prepared from 0.66 g. of copper pentyne, 2.5 ml. of tri-n-butylphosphine, and 6.5 ml. of ether. The solution is stirred at −78° C. for 90 minutes and then treated with a solution of 1.83 g. of 2-(7',8'-trimethylsilyloxy-2-cis-octenyl)-4-trimethylsilyloxycyclopent-2-en-1-one (Preparation 12) in 7.5 ml. of ether during 10 minutes. The solution is stirred at −45° to −40° C. for 60 and −40° to −35° C. for 45 minutes. The solution is recooled to −78° C. and quenched with a solution of 0.60 ml. of acetic acid in 10 ml. of ether. The solution is poured into a stirred mixture of ether and saturated ammonium chloride. The organic layer is separated and washed successively with water and brine, dried over magnesium sulfate, and concentrated.

The residue is treated with 32 ml. of acetic acid, 16 ml. of tetrahydrofuran, and 8 ml. of water, and the resulting solution is stirred at 40° C. for one hour. The solution is partitioned with half-saturated brine and ethyl acetate. The organic layer is washed with brine, dried over magnesium sulfate, and concentrated. The residue is partitioned between n-heptane and 50:1 methanol-water.

The methanol phase is concentrated to give the crude product which is subjected to column chromatography on silica gel to give an oil.

EXAMPLE 3

11α,16-Dihydroxy-1-hydroxymethyl-16-vinyl-9-oxo-5-cis-13-trans-prostadien-1-ol

A stirred solution of 3.54 g. of (4-trimethylsiloxy-4-vinyl-1-trans-octenyl)tributylstannane in 5.0 ml. of tetrahydrofuran is treated with 3.43 ml. of 2.2 M. n-butyllithium in hexane at −78° C. The resulting solution is allowed to warm to −23° C. over a period of 2 hours, is recooled to −78° C., and then treated with a solution prepared from 0.90 g. of copper pentyne, 2.39 ml. of hexamethylphosphoroustriamide, and 5 ml. of tetrahydrofuran. The resulting solution is stirred at −78° C. for 70 minutes and then treated with a solution of 2.41 g. of 2-(7′,8′-bistrimethylsilyloxy-2-cis-octenyl)-4-trimethylsilyloxycyclopent-2-en-1-one (Preparation 12) in 10 ml. of tetrahydrofuran during 5 minutes. The resulting solution is stirred at −78° C. for 20 minutes, at −30° C. for 90 minutes, and is recooled to −45° C. and poured into a stirred, ice-cold mixture of 200 ml. of saturated ammonium chloride and 100 ml of ether. The ether phase is separated and washed successively with cold 5% hydrochloric acid and brine, dried over magnesium sulfate, and concentrated.

The resulting oil is treated with a mixture of 50 ml. of acetic acid, 25 ml. of tetrahydrofuran, and 12.5 ml. of water. The resulting mixture is stirred at 25° C. for 60 minutes diluted with toluene, and evaporated under vacuum. The residue is washed with hexane to remove tetrabutylstannane by decantation, and the oil remaining is subjected to chromatography on silica gel to give an oil.

EXAMPLE 4

3β-[3-(1-Butylcyclobutyl)-3-hydroxy-1-propenyl]-2α-(7,8-dihydroxy-2-octenyl)-4α-hydroxycyclopentanone A stirred solution of 2.11 g. of E-1-iodo-4,4-trimethylenyl-3-trimethylsilyloxy-1-octene in 10 ml. of ether is cooled in a dry ice-acetone bath under argon and treated with 7.2 ml. of 1.6 M. t-butyllithium in pentane over a 5 minute period. After 20 minutes at −78° C. the mixture is placed in a salt-ice bath and raised to −15° C. over a 10 minute period. The mixture is allowed to remain at −15° C. for one hour, then is recooled to −78° C. A solution of 0.75 g. of pentynyl copper in 2.6 ml. of hexamethylphosphoroustriamide is added over a 10 minute period and the mixture is allowed to stand at −78° C. for one hour and 35 minutes. A solution of 2-(7′,8′-bis-trimethylsilyloxy-2-cis-octenyl)-4-trimethylsilyloxycyclopent-2-en-1-one (Preparation 12) in 10 ml. of ether is added over a 10 minute period and stirring is continued at −78° C. for 30 minutes. The mixture is warmed to −45° C. over a 14 minute period, maintained at −45° to −40° for one hour, then −40° to −35° C. for one hour, recooled to −78° C. and quenched with 0.8 ml. of glacial acetic acid in 10 ml. of ether. The mixture is poured into 150 ml. of ice-cold saturated ammonium chloride and 100 ml. of ether with vigorous stirring, stirred for 30 minutes and refrigerated for 2 days. The aqueous phase is extracted three times with ether. The organic phases are combined and washed with six 50 ml. portions of cold 1% sulfuric acid and three times with saturated saline, dried over magnesium sulfate, filtered through Celite and evaporated in vacuo to an amber oil.

This oil is combined with 40 ml. of glacial acetic acid, 20 ml. of tetrahydrofuran and 10 ml. of water and stirred at 40° C., under argon, for one hour. The mixture is poured into saturated saline, extracted three times with ethyl acetate, washed three times with saturated saline, dried over magnesium sulfate, filtered through Celite and evaporated in vacuo to an oil. This oil is subjected to conventional chromatography to give 763 mg. of the desired product.

EXAMPLE 5

3β-(4-Butylhydroxy-4-hydroxyl-1,5-hexadienyl)-2α-(7,8-dihydroxyoctyl)-4α-hydroxycyclopentanone A solution of 5.16 g. of E-1-tri-n-butylstannyl-4-trimethylsilyloxy-4-vinyl-1-octene in 8.0 ml. of tetrahydrofuran is treated with 3.2 ml. of 2.5 M. n-butyllithium in hexane at −78° C. The reaction is warmed to −40° C. for 90 minutes, then to −30° C. for 10 minutes. A solution of 1.16 g. of pentynyl copper in 3.2 ml. of hexamethyl phosphorous triamide and 10 ml. of ether is added at −78° C. A solution of 1.84 g. of 8-(4-hydroxycyclopent-2-en-1-on-2-yl)-1,2-octanediol in 10 ml. of ether is added at −78° C. The reaction is continued at −45° to −40° C. for 60 minutes, then at −40° to −35° C. for 60 minutes, recooled to −78° C. and quenched with a solution of 1 ml. of glacial acetic acid in 10 ml. of ether. The mixture is washed repeatedly with water, saturated sodium bicarbonate and brine and then evaporated to a light yellow oil.

This oil is combined with 32 ml. of glacial acetic acid, 16 ml. of tetrahydrofuran and 8 ml. of water and stirred at 25° C. for 90 minutes. The mixture is diluted with 75 ml. of ethyl acetate and 60 ml. of half saturated brine. The ethyl acetate phase is separated, washed with two 50 ml. portions of half saturated brine, then two 50 ml. portions of brine, dried over magnesium sulfate and evaporated to an oil. This oil is subjected to conventional chromatography giving 0.97 g. of the desired product as a light amber oil.

| EXAMPLE | VINYL TIN | CYCLOPENTENONE | PRODUCT PROSTAGLANDIN OF THE 11-DEOXY PGE1 SERIES |
|---|---|---|---|
| 6 | 1-trans-tri-n-butylstannyl-4-cyclopropyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-cyclopropyl-2-nor-13-trans prostene |
| 7 | 1-trans-tri-n-butylstannyl-4-trimethylsilylethynyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-ethynyl-20-nor-2-nor-13-trans prostene |
| 8 | 1-trans-tri-n-butylstannyl-5-methylene-4-triethylsilyloxy-1-heptene | 2-(6,7-bis-trimethylsilyloxyheptyl)cyclopent-2-en-1-one | dl-1,16-dihydroxy-1-hydroxymethyl-9-oxo-17-methylene-20-nor-2-nor-13-trans prostene |
| 9 | 1-trans-tri-n-butylstannyl-4-methyl-5-methylene-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-methyl-17-methylene-20-nor-2-nor-13-trans prostene |
| 10 | 1-trans-tri-n-butylstannyl-4-dimethoxymethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-formyl-20-nor-2-nor-13-trans prostene |
| 11 | 1-trans-tri-n-butylstannyl-4-fluoromethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-fluoromethyl-20-nor-2-nor-13-trans prostene |
| 12 | 1-trans-tri-n-butylstannyl-4-difluoromethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-difluoromethyl-20-nor-2-nor-13-trans prostene |
| 13 | 1-trans-tri-n-butylstannyl-4-trifluoromethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-trifluoromethyl-20-nor-2-nor-13-trans prostene |
| 14 | 1-trans-tri-n-butylstannyl-4-chloromethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-chloromethyl-20-nor-2-nor-13-trans prostene |
| 15 | 1-trans-tri-n-butylstannyl-4-trimethylsilyloxymethyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-hydroxymethyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 16 | 1-trans-iodo-4-methyl-7-chloro-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-methyl-19-chloro-2-nor-20-nor-13-trans prostene |
| 17 | 1-trans-iodo-4-triphenylmethoxy-1-heptene | 2-(6,7-bis-trimethylsilyloxyheptyl)cyclopent-2-en-1-one | dl-1,16-dihydroxy-1-hydroxymethyl-9-oxo-20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 18 | 1-trans-tri-n-butylstannyl-4-trimethylsilyloxymethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-hydroxymethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 19 | 1-trans-iodo-4-triphenylmethoxy-1-octene | 2-(6,7-bis-trimethylsilyloxyheptyl)cyclopent-2-en-1-one | dl-1,16-dihydroxy-1-hydroxymethyl-9-oxo-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 20 | 1-trans-tri-n-butylstannyl-4-methyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-methyl-2-nor-13-trans prostene |
| 21 | 1-trans-tri-n-butylstannyl-4-methyl-5-methyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-17-methyl-2-nor-13-trans prostene |
| 22 | 1-trans-tri-n-butylstannyl-4-vinyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-vinyl-2-nor-13-trans prostene |
| 23 | 1-trans-tri-n-butylstannyl-4-trimethylsilylethynyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-ethynyl-2-nor-13-trans prostene |
| 24 | 1-trans-tri-n-butylstannyl-5-methylene-4-triethylsilyloxy-1-octene | 2-(6,7-bis-trimethylsilyloxyheptyl)cyclopent-2-en-1-one | dl-1,16-dihydroxy-1-hydroxymethyl-9-oxo-17-methylene-2-nor-13-trans prostene |
| 25 | 1-trans-tri-n-butylstannyl-4-methyl-5-methylene-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-methyl-17-methylene-2-nor-13-trans prostene |
| 26 | 1-trans-tri-n-butylstannyl-4-dimethoxymethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-formyl-2-nor-13-trans prostene |
| 27 | 1-trans-tri-n-butylstannyl-4-fluoromethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-fluoromethyl-2-nor-13-trans prostene |

| | -continued | | |
|---|---|---|---|
| 28 | 1-trans-tri-n-butylstannyl-4-difluoromethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-difluoromethyl-2-nor-13-trans prostene |
| 29 | 1-trans-tri-n-butylstannyl-4-trifluoromethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-trifluoromethyl-2-nor-13-trans prostene |
| 30 | 1-trans-tri-n-butylstannyl-4-chloromethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-chloromethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 31 | 1-trans-iodo-4-triphenylmethoxy-1-nonene | 2-(6,7-bis-trimethylsilyloxyheptyl)cyclopent-2-en-1-one | dl-1,16-dihydroxy-1-hydroxymethyl-9-oxo-20-methyl-2-nor-13-trans prostene |
| EXAMPLE | VINYL TIN | CYCLOPENTENONE | PRODUCT PROSTAGLANDIN OF THE 11-DEOXY PGE1 SERIES |
| 32 | 1-trans-tri-n-butylstannyl-4-methyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-methyl-20-methyl-2-nor-13-trans prostene |
| 33 | 1-trans-tri-n-butylstannyl-4-methyl-5-methyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-17-methyl-20-methyl-2-nor-13-trans prostene |
| 34 | 1-trans-tri-n-butylstannyl-4-vinyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-vinyl-20-methyl-2-nor-13-trans prostene |
| 35 | 1-trans-tri-n-butylstannyl-4-trimethylsilylethynyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-ethynyl-20-methyl-2-nor-13-trans prostene |
| 36 | 1-trans-tri-n-butylstannyl-5-methylene-4-triethylsilyloxy-1-nonene | 2-(6,7-bis-trimethylsilyloxyheptyl)cyclopent-2-en-1-one | dl-1,16-dihydroxy-1-hydroxymethyl-9-oxo-17-methylene-20-methyl-2-nor-13-trans prostene |
| 37 | 1-trans-tri-n-butylstannyl-4-methyl-5-methylene-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-methyl-17-methylene-20-methyl-2-nor-13-trans prostene |
| 38 | 1-trans-tri-n-butylstannyl-4-dimethoxymethyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-formyl-20-methyl-2-nor-13-trans prostene |
| 39 | 1-trans-tri-n-butylstannyl-4-fluoromethyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-fluoromethyl-20-methyl-2-nor-13-trans prostene |
| 40 | 1-trans-tri-n-butylstannyl-4-difluoromethyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-difluoromethyl-20-methyl-2-nor-13-trans prostene |
| 41 | 1-trans-tri-n-butylstannyl-4-trifluoromethyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-trifluoromethyl-20-methyl-2-nor-13-trans prostene |
| 42 | 1-trans-tri-n-butylstannyl-4-chloromethyl-4-trimethylsilyloxy-1-nonene | 2-(6,7-bis-trimethylsilyloxyheptyl)cyclopent-2-en-1-one | dl-1,16-dihydroxy-1-hydroxymethyl-9-oxo-16-chloromethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 43 | 1-trans-iodo-4-triphenylmethoxy-1-decene | 2-(6,7-bis-trimethylsilyloxyheptyl)cyclopent-2-en-1-one | dl-1,16-dihydroxy-1-hydroxymethyl-9-oxo-20-ethyl-2-nor-13-trans prostene |
| EXAMPLE | VINYL TIN | CYCLOPENTENONE | PRODUCT PROSTAGLANDIN OF THE 11-DEOXY PGE1 SERIES |
| 44 | 1-trans-tri-n-butylstannyl-4-methyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-methyl-20-ethyl-2-nor-13-trans prostene |
| 45 | 1-trans-tri-n-butylstannyl-4-methyl-5-methyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-17-methyl-20-ethyl-2-nor-13-trans prostene |
| 46 | 1-trans-tri-n-butylstannyl-4-vinyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-vinyl-20-ethyl-2-nor-13-trans prostene |
| 47 | 1-trans-tri-n-butylstannyl-4-trimethylsilylethynyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-ethynyl-20-ethyl-2-nor-13-trans prostene |
| 48 | 1-trans-tri-n-butylstannyl-5-methylene-4-triethylsilyloxy-1-decene | 2-(6,7-bis-trimethylsilyloxyheptyl)cyclopent-2-en-1-one | dl-1,16-dihydroxy-1-hydroxymethyl-9-oxo-17-methylene-20-ethyl-2-nor-13-trans prostene |
| 49 | 1-trans-tri-n-butylstannyl-4-methyl-5-methylene-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-methyl-17-methylene-20-ethyl-2-nor-13-trans prostene |
| 50 | 1-trans-tri-n-butylstannyl-4-dimethoxymethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-formyl-20-ethyl-2-nor-13-trans prostene |

| | -continued | | |
|---|---|---|---|
| 51 | 4-trimethylsilyloxy-1-decene | 2-(6,7-bis-trimethylsilyloxyheptyl)cyclopent-2-en-1-one | 20-ethyl-2-nor-13-trans prostene |
| | 1-trans-tri-n-butylstannyl-4-fluoromethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-fluoromethyl-20-ethyl-2-nor-13-trans prostene |
| 52 | 1-trans-tri-n-butylstannyl-4-difluoromethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-difluoromethyl-20-ethyl-2-nor-13-trans prostene |
| 53 | 1-trans-tri-n-butylstannyl-4-trifluoromethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-trifluoromethyl-20-ethyl-2-nor-13-trans prostene |
| 54 | 1-trans-tri-n-butylstannyl-4-chloromethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-chloromethyl-20-ethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 55 | 1-trans-iodo-4-triphenylmethoxy-1-heptene | 2-(7,8-bis-trimethylsilyloxyoctyl)cyclopent-2-en-1-one | dl-1,16-dihydroxy-1-hydroxymethyl-9-oxo-20-nor-13-trans prostene |
| EXAMPLE | VINYL TIN | CYCLOPENTENONE | PRODUCT PROSTAGLANDIN OF THE 11-DEOXY PGE1 SERIES |
| 56 | 1-trans-tri-n-butylstannyl-4-methyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-methyl-20-nor-13-trans prostene |
| 57 | 1-trans-tri-n-butylstannyl-4-trimethylsilyloxymethyl-4-trimethylsilyloxy-1-decene | 2-(6,7-bis-trimethylsilyloxyheptyl)cyclopent-2-en-1-one | dl-1,16-dihydroxy-1-hydroxymethyl-9-oxo-16-hydroxymethyl-20-ethyl-2-nor-13-trans prostene |
| 58 | 1-trans-tri-n-butylstannyl-4-fluoromethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-fluoromethyl-20-nor-13-trans prostene |
| 59 | 1-trans-tri-n-butylstannyl-4-difluoromethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-difluoromethyl-20-nor-13-trans prostene |
| 60 | 1-trans-tri-n-butylstannyl-4-trifluoromethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-trifluoromethyl-20-nor-13-trans prostene |
| 61 | 1-trans-tri-n-butylstannyl-4-chloromethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-chloromethyl-20-nor-13-trans prostene |
| 62 | 1-trans-tri-n-butylstannyl-4-trimethylsilyloxymethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-hydroxymethyl-20-nor-13-trans prostene |
| EXAMPLE | VINYL IODIDE | CYCLOPENTENONE | PRODUCT PROSTAGLANDIN OF THE 11-DEOXY PGE1 SERIES |
| 63 | 1-trans-iodo-4-methyl-7-chloro-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-methyl-19-chloro-20-nor-13-trans prostene |
| EXAMPLE | VINYL TIN | CYCLOPENTENONE | PRODUCT PROSTAGLANDIN OF THE 11-DEOXY PGE1 SERIES |
| 64 | 1-trans-tri-n-butylstannyl-5-methylene-4-triethylsilyloxy-1-heptene | 2-(7,8-bis-trimethylsilyloxyoctyl)cyclopent-2-en-1-one | dl-1,16-dihydroxy-1-hydroxymethyl-9-oxo-17-methylene-20-nor-13-trans prostene |
| 65 | 1-trans-tri-n-butylstannyl-4-methyl-5-methylene-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-methyl-17-methylene-20-nor-13-trans prostene |
| 66 | 1-trans-tri-n-butylstannyl-4-dimethoxymethyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-formyl-20-nor-13-trans prostene |
| 67 | 1-trans-tri-n-butylstannyl-4-vinyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-vinyl-20-nor-13-trans prostene |
| 68 | 1-trans-tri-n-butylstannyl-4-cyclopropyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-cyclopropyl-13-trans prostene |
| 69 | 1-trans-tri-n-butylstannyl-4-trimethylsilylethynyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-16-ethynyl-20-nor-13-trans prostene |
| 70 | 1-trans-tri-n-butylstannyl-4-ethyl-4-trimethylsilyloxy-1-octene | 2-(7,8-bis-trimethylsilyloxyoctyl)cyclopent-2-en-1-one | dl-1,16-dihydroxy-1-hydroxymethyl-9-oxo-16-ethyl-13-trans prostene |
| 71 | 1-trans-tri-n-butylstannyl-5-methyl-4-trimethylsilyloxy-1-heptene | 2-(7,8-bis-trimethylsilyloxyoctyl)cyclopent-2-en-1-one | dl-1,16-dihydroxy-1-hydroxymethyl-9-oxo-17-methyl-20-nor-13-trans prostene |
| EXAMPLE | VINYL IODIDE | CYCLOPENTENONE | PRODUCT PROSTAGLANDIN OF THE 11-DEOXY PGE1 SERIES |

-continued

| EXAMPLE | VINYL IODIDE | CYCLOPENTENONE | PRODUCT PROSTAGLANDIN OF THE 11-DEOXY PGE1 SERIES |
|---|---|---|---|
| 72 | 1-trans-iodo-5,5-dimethyl 4-trimethylsilyloxy-1-octene | 2-(7,8-bis-trimethylsilyloxyoctyl) cyclopent-2-en-1-one | dl-1,16-dihydroxy-1-hydroxymethyl-9-oxo-17,17-dimethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 73 | 1-trans-tri-n-butylstannyl-4-methyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-methyl-13-trans prostene |
| 74 | 1-trans-tri-n-butylstannyl-5-methyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-17-methyl-13-trans prostene |
| 75 | 1-trans-tri-n-butylstannyl-4-vinyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-vinyl-13-trans prostene |
| 76 | 1-trans-tri-n-butylstannyl-4-trimethylsilylethynyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-ethynyl-13-trans prostene |
| 77 | 1-trans-tri-n-butylstannyl-5-methylene-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-17-methylene-13-trans prostene |
| 78 | 1-trans-tri-n-butylstannyl-4-methyl-5-methylene-4-triethylsilyloxy-1-octene | 2-(7,8-bis-trimethylsilyloxyoctyl) cyclopent-2-en-1-one | dl-1,16-dihydroxy-1-hydroxymethyl-9-oxo-16-methyl-17-methylene-13-trans prostene |
| 79 | 1-trans-tri-n-butylstannyl-4-dimethoxymethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-formyl-13-trans prostene |
| 80 | 1-trans-tri-n-butylstannyl-4-fluoromethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-fluoromethyl-13-trans prostene |
| 81 | 1-trans-tri-n-butylstannyl-4-difluoromethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-difluoromethyl-13-trans prostene |
| 82 | 1-trans-tri-n-butylstannyl-4-trifluoromethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-trifluoromethyl-13-trans prostene |
| 83 | 1-trans-tri-n-butylstannyl-4-chloromethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-chloromethyl-13-trans prostene |
| 84 | 1-trans-tri-n-butylstannyl-4-trimethylsilyloxymethyl-4-trimethylsilyloxy-1-octene | 2-(7,8-bis-trimethylsilyloxyoctyl) cyclopent-2-en-1-one | dl-1,16-dihydroxy-1-hydroxymethyl-9-oxo-16-hydroxymethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 85 | 1-trans-iodo-4-triphenylmethoxy-1-nonene | 2-(7,8-bis-trimethylsilyloxyoctyl) cyclopent-2-en-1-one | dl-1,16-dihydroxy-1-hydroxymethyl-9-oxo-20-methyl-2-nor-13-trans prostene |
| 86 | 1-trans-iodo-4-triphenylmethoxy-1-octene | 2-(7,8-bis-trimethylsilyloxyoctyl) cyclopent-2-en-1-one | dl-1,16-dihydroxy-1-hydroxymethyl-9-oxo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 87 | 1-trans-tri-n-butylstannyl-4-trimethylsilyloxymethyl-4-trimethylsilyloxy-1-nonene | 2-(6,7-bis-trimethylsilyloxyheptyl) cyclopent-2-en-1-one | dl-1,16-dihydroxy-1-hydroxymethyl-9-oxo-16-hydroxymethyl-20-methyl-2-nor-13-trans prostene |
| 88 | 1-trans-tri-n-butylstannyl-4-trifluoromethyl-4-trimethylsilyloxy-1-nonene | 2-(7,8-bis-trimethylsilyloxyoctyl) cyclopent-2-en-1-one | dl-1,16-dihydroxy-1-hydroxymethyl-9-oxo-16-trifluoromethyl-20-methyl-13-trans prostene |
| 89 | 1-trans-tri-n-butylstannyl-4-chloromethyl-4-trimethylsilyloxy-1-nonene | 2-(7,8-bis-trimethylsilyloxyoctyl) cyclopent-2-en-1-one | dl-1,16-dihydroxy-1-hydroxymethyl-9-oxo-16-chloromethyl-20-methyl-13-trans prostene |
| 90 | 1-trans-tri-n-butylstannyl-4-trimethylsilylethynyl-4-trimethylsilyloxy-1-nonene | 2-(7,8-bis-trimethylsilyloxyoctyl) cyclopent-2-en-1-one | dl-1,16-dihydroxy-1-hydroxymethyl-9-oxo-16-hydroxymethyl-20-methyl-13-trans prostene |
| 91 | 1-trans-tri-n-butylstannyl-4-trimethylsilyloxy-1-nonene | 2-(7,8-bis-trimethylsilyloxyoct-2-cis-enyl) cyclopent-2-en-1-one | dl-1,16-dihydroxy-1-hydroxymethyl-9-oxo-16-ethynyl-20-methyl-5-cis-13-trans prostadiene |
| 92 | 1-trans-tri-n-butylstannyl-5-methylene-4-trimethylsilyloxy-1-nonene | 2-(7,8-bis-trimethylsilyloxyoct-2-cis-enyl) cyclopent-2-en-1-one | dl-1,16-dihydroxy-1-hydroxymethyl-9-oxo-17-methylene-20-methyl-5-cis-13-trans prostadiene |
| 93 | 1-trans-tri-n-butylstannyl-4-methyl-5-methylene-4-triethylsilyloxy-1-nonene | 2-(7,8-bis-trimethylsilyloxyoct-2-cis-enyl) cyclopent-2-en-1-one | dl-1,16-dihydroxy-1-hydroxymethyl-9-oxo-16-methyl-17-methylene-20-methyl-5-cis-13-trans prostadiene |
| 94 | 1-trans-tri-n-butylstannyl-4-trimethylsilylethynyl-4-trimethylsilyloxy-1-nonene | 2-(7,8-bis-trimethylsilyloxyoctyl) cyclopent-2-en-1-one | dl-1,16-dihydroxy-1-hydroxymethyl-9-oxo-16-ethynyl-20-methyl-13-trans prostene |
| 95 | 1-trans-tri-n-butylstannyl-5-methylene-4-trimethylsilyloxy-1-nonene | 2-(7,8-bis-trimethylsilyloxyoctyl) cyclopent-2-en-1-one | dl-1,16-dihydroxy-1-hydroxymethyl-9-oxo-17-methylene- |

-continued

| | | | |
|---|---|---|---|
| 96 | 4-triethylsilyloxy-1-nonene | cyclopent-2-en-1-one | 20-methyl-13-trans prostene |
| | 1-trans-tri-n-butylstannyl-4-methyl-5-methylene | 2-(7,8-bis-trimethylsilyloxyoctyl) | dl-1,16-dihydroxy-1-hydroxymethyl-9-oxo-16-methyl-17-methylene- |
| | 4-trimethylsilyloxy-1-nonene | cyclopent-2-en-1-one | 20-methyl-13-trans prostene |
| 97 | 1-trans-tri-n-butylstannyl-4-methyl- | 2-(7,8-bis-trimethylsilyloxyoctyl) | dl-1,16-dihydroxy-1-hydroxymethyl-9-oxo-16-methyl- |
| | 4-trimethylsilyloxy-1-nonene | cyclopent-2-en-1-one | 20-methyl-13-trans prostene |
| 98 | 1-trans-tri-n-butylstannyl-5-methyl | 2-(7,8-bis-trimethylsilyloxyoctyl) | dl-1,16-dihydroxy-1-hydroxymethyl-9-oxo-17-methyl- |
| | 4-trimethylsilyloxy-1-nonene | cyclopent-2-en-1-one | 20-methyl-13-trans prostene |
| 99 | 1-trans-tri-n-butylstannyl-4-vinyl- | 2-(7,8-bis-trimethylsilyloxyoctyl) | dl-1,16-dihydroxy-1-hydroxymethyl-9-oxo-16-vinyl- |
| | 4-trimethylsilyloxy-1-nonene | cyclopent-2-en-1-one | 20-methyl-13-trans prostene |
| 100 | 1-trans-tri-n-butylstannyl-4-trifluoromethyl- | 2-(7,8-bis-trimethylsilyloxyoctyl) | dl-1,16-dihydroxy-1-hydroxymethyl-9-oxo-16-trifluoromethyl- |
| | 4-trimethylsilyloxy-1-decene | cyclopent-2-en-1-one | 20-ethyl-13-trans prostene |
| 101 | 1-trans-tri-n-butylstannyl-4-chloromethyl- | 2-(7,8-bis-trimethylsilyloxyoctyl) | dl-1,16-dihydroxy-1-hydroxymethyl-9-oxo-16-chloromethyl- |
| | 4-trimethylsilyloxy-1-decene | cyclopent-2-en-1-one | 20-ethyl-13-trans prostene |
| 102 | 1-trans-tri-n-butylstannyl-4-trimethylsilyloxymethyl- | 2-(7,8-bis-trimethylsilyloxyoctyl) | dl-1,16-dihydroxy-1-hydroxymethyl-9-oxo-16-hydroxymethyl- |
| | 4-trimethylsilyloxy-1-decene | cyclopent-2-en-1-one | 20-ethyl-13-trans prostene |
| 103 | 1-trans-tri-n-butylstannyl-4-dimethoxymethyl- | 2-(7,8-bis-trimethylsilyloxyoctyl) | dl-1,16-dihydroxy-1-hydroxymethyl-9-oxo-16-formyl- |
| | 4-trimethylsilyloxy-1-decene | cyclopent-2-en-1-one | 20-ethyl-13-trans prostene |
| 104 | 1-trans-tri-n-butylstannyl-4-fluoromethyl- | 2-(7,8-bis-trimethylsilyloxyoctyl) | dl-1,16-dihydroxy-1-hydroxymethyl-9-oxo-16-fluoromethyl- |
| | 4-trimethylsilyloxy-1-decene | cyclopent-2-en-1-one | 20-ethyl-13-trans prostene |
| 105 | 1-trans-tri-n-butylstannyl-4-difluoromethyl- | 2-(7,8-bis-trimethylsilyloxyoctyl) | dl-1,16-dihydroxy-1-hydroxymethyl-9-oxo-16-difluoromethyl- |
| | 4-trimethylsilyloxy-1-decene | cyclopent-2-en-1-one | 20-ethyl-13-trans prostene |
| 106 | 1-trans-tri-n-butylstannyl-4-trimethylsilylethynyl- | 2-(7,8-bis-trimethylsilyloxyoctyl) | dl-1,16-dihydroxy-1-hydroxymethyl-9-oxo-16-ethynyl- |
| | 4-trimethylsilyloxy-1-decene | cyclopent-2-en-1-one | 20-ethyl-13-trans prostene |
| 107 | 1-triethylsilyloxy-1-decene | 2-(7,8-bis-trimethylsilyloxyoctyl) | dl-1,16-dihydroxy-1-hydroxymethyl-9-oxo-17-methylene- |
| | 4-triethylsilyloxy-1-decene | cyclopent-2-en-1-one | 20-ethyl-13-trans prostene |
| 108 | 1-trans-tri-n-butylstannyl-4-methyl-5-methylene | 2-(7,8-bis-trimethylsilyloxyoctyl) | dl-1,16-dihydroxy-1-hydroxymethyl-9-oxo-16-methyl-17-methylene- |
| | 4-trimethylsilyloxy-1-decene | cyclopent-2-en-1-one | 20-ethyl-13-trans prostene |
| 109 | 1-trans-tri-n-butylstannyl-4-methyl- | 2-(7,8-bis-trimethylsilyloxyoctyl) | dl-1,16-dihydroxy-1-hydroxymethyl-9-oxo-16-methyl- |
| | 4-trimethylsilyloxy-1-decene | cyclopent-2-en-1-one | 20-ethyl-13-trans prostene |
| 110 | 1-trans-tri-n-butylstannyl-5-methyl- | 2-(7,8-bis-trimethylsilyloxyoctyl) | dl-1,16-dihydroxy-1-hydroxymethyl-9-oxo-17-methyl- |
| | 4-trimethylsilyloxy-1-decene | cyclopent-2-en-1-one | 20-ethyl-13-trans prostene |
| 111 | 1-trans-tri-n-butylstannyl-4-vinyl- | 2-(7,8-bis-trimethylsilyloxyoctyl) | dl-1,16-dihydroxy-1-hydroxymethyl-9-oxo-16-vinyl- |
| | 4-trimethylsilyloxy-1-decene | cyclopent-2-en-1-one | 20-ethyl-13-trans prostene |
| 112 | 1-trans-tri-n-butylstannyl-4-trimethylsilyloxymethyl- | 2-(8,9-bis-trimethylsilyloxynonyl) | dl-1,16-dihydroxy-1-hydroxymethyl-9-oxo-16-hydroxymethyl- |
| | 4-trimethylsilyloxy-1-heptene | cyclopent-2-en-1-one | 20-nor-2-homo-13-trans prostene |
| EXAMPLE | VINYL IODIDE | CYCLOPENTENONE | PRODUCT PROSTAGLANDIN OF THE 11-DEOXY PGE1 SERIES |
| 113 | 1-trans-iodo-4-methyl-7-chloro | 2-(8,9-bis-trimethylsilyloxynonyl) | dl-1,16-dihydroxy-1-hydroxymethyl-9-oxo-16-methyl-19-chloro- |
| | 4-trimethylsilyloxy-1-heptene | cyclopent-2-en-1-one | 2-homo-20-nor-13-trans prostene |
| 114 | 1-iodo- | 2-(8,9-bis-trimethylsilyloxynonyl) | dl-1,16-dihydroxy-1-hydroxymethyl-9-oxo- |
| | 4-triphenylmethoxy-1-decene | cyclopent-2-en-1-one | 20-ethyl-13-trans prostene |
| EXAMPLE | VINYL TIN | CYCLOPENTENONE | PRODUCT PROSTAGLANDIN OF THE 11-DEOXY PGE1 SERIES |
| 115 | 1-trans-tri-n-butylstannyl-4-difluoromethyl- | 2-(8,9-bis-trimethylsilyloxynonyl) | dl-1,16-dihydroxy-1-hydroxymethyl-9-oxo-16-difluoromethyl- |
| | 4-trimethylsilyloxy-1-heptene | cyclopent-2-en-1-one | 20-nor-2-homo-13-trans prostene |
| 116 | 1-trans-tri-n-butylstannyl-4-trifluoromethyl- | 2-(8,9-bis-trimethylsilyloxynonyl) | dl-1,16-dihydroxy-1-hydroxymethyl-9-oxo-16-trifluoromethyl- |
| | 4-trimethylsilyloxy-1-heptene | cyclopent-2-en-1-one | 20-nor-2-homo-13-trans prostene |
| 117 | 1-trans-tri-n-butylstannyl-4-chloromethyl- | 2-(8,9-bis-trimethylsilyloxynonyl) | dl-1,16-dihydroxy-1-hydroxymethyl-9-oxo-16-chloromethyl- |
| | 4-trimethylsilyloxy-1-heptene | cyclopent-2-en-1-one | 20-nor-2-homo-13-trans prostene |
| 118 | 1-trans-tri-n-butylstannyl-4-methyl-5-methylene | 2-(8,9-bis-trimethylsilyloxynonyl) | dl-1,16-dihydroxy-1-hydroxymethyl-9-oxo-16-methyl-17-methylene- |
| | 4-trimethylsilyloxy-1-heptene | cyclopent-2-en-1-one | 20-nor-2-homo-13-trans prostene |
| 119 | 1-trans-tri-n-butylstannyl-4-dimethoxymethyl- | 2-(8,9-bis-trimethylsilyloxynonyl) | dl-1,16-dihydroxy-1-hydroxymethyl-9-oxo-16-formyl- |
| | 4-trimethylsilyloxy-1-heptene | cyclopent-2-en-1-one | 20-nor-2-homo-13-trans prostene |

| | VINYL IODIDE | CYCLOPENTENONE | PRODUCT PROSTAGLANDIN OF THE 11-DEOXY PGE1 SERIES |
|---|---|---|---|
| 120 | 1-trans-tri-n-butylstannyl-4-fluoromethyl-4-trimethylsilyloxy-1-heptene | 2-(8,9-bis-trimethylsilyloxynonyl)cyclopent-2-en-1-one | dl-1,16-dihydroxy-1-hydroxymethyl-9-oxo-16-fluoromethyl-20-nor-2-homo-13-trans prostene |
| 121 | 1-trans-tri-n-butylstannyl-4-cyclopropyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-cyclopropyl-2-homo-13-trans prostene |
| 122 | 1-trans-tri-n-butylstannyl-4-trimethylsilylethynyl-4-trimethylsilyloxy-1-heptene | 2-(8,9-bis-trimethylsilyloxynonyl)cyclopent-2-en-1-one | dl-1,16-dihydroxy-1-hydroxymethyl-9-oxo-16-ethynyl-20-nor-2-homo-13-trans prostene |
| 123 | 1-trans-tri-n-butylstannyl-5-methylene-4-triethylsilyloxy-1-heptene | 2-(8,9-bis-trimethylsilyloxynonyl)cyclopent-2-en-1-one | dl-1,16-dihydroxy-1-hydroxymethyl-9-oxo-17-methylene-20-nor-2-homo-13-trans prostene |
| 124 | 1-trans-tri-n-butylstannyl-5-methyl-4-trimethylsilyloxy-1-heptene | 2-(8,9-bis-trimethylsilyloxynonyl)cyclopent-2-en-1-one | dl-1,16-dihydroxy-1-hydroxymethyl-9-oxo-17-methyl-20-nor-2-homo-13-trans prostene |
| EXAMPLE | VINYL IODIDE | CYCLOPENTENONE | PRODUCT PROSTAGLANDIN OF THE 11-DEOXY PGE1 SERIES |
| 125 | 1-iodo-5,5-dimethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-17,17-dimethyl-2-homo-13-trans prostene |
| EXAMPLE | VINYL TIN | CYCLOPENTENONE | PRODUCT PROSTAGLANDIN OF THE 11-DEOXY PGE1 SERIES |
| 126 | 1-trans-tri-n-butylstannyl-4-vinyl-4-trimethylsilyloxy-1-heptene | 2-(8,9-bis-trimethylsilyloxynonyl)cyclopent-2-en-1-one | dl-1,16-dihydroxy-1-hydroxymethyl-9-oxo-16-vinyl-20-nor-2-homo-13-trans prostene |
| EXAMPLE | VINYL IODIDE | CYCLOPENTENONE | PRODUCT PROSTAGLANDIN OF THE 11-DEOXY PGE1 SERIES |
| 127 | 1-iodo-4-triphenylmethoxy-1-heptene | 2-(8,9-bis-trimethylsilyloxynonyl)cyclopent-2-en-1-one | dl-1,16-dihydroxy-1-hydroxymethyl-9-oxo-20-nor-2-homo-13-trans prostene |
| EXAMPLE | VINYL TIN | CYCLOPENTENONE | PRODUCT PROSTAGLANDIN OF THE 11-DEOXY PGE1 SERIES |
| 128 | 1-trans-tri-n-butylstannyl-4-methyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-methyl-2-homo-13-trans prostene |
| 129 | 1-trans-tri-n-butylstannyl-4-ethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-ethyl-2-homo-13-trans prostene |
| 130 | 1-trans-tri-n-butylstannyl-5-methyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-17-methyl-2-homo-13-trans prostene |
| 131 | 1-trans-tri-n-butylstannyl-4-vinyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-vinyl-2-homo-13-trans prostene |
| 132 | 1-trans-tri-n-butylstannyl-4-trimethylsilylethynyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-ethynyl-2-homo-13-trans prostene |
| 133 | 1-trans-tri-n-butylstannyl-5-methylene-4-triethylsilyloxy-1-octene | 2-(8,9-bis-trimethylsilyloxynonyl)cyclopent-2-en-1-one | dl-1,16-dihydroxy-1-hydroxymethyl-9-oxo-17-methylene-2-homo-13-trans prostene |
| 134 | 1-trans-tri-n-butylstannyl-4-methyl-5-methylene-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-methyl-17-methylene-2-homo-13-trans prostene |
| 135 | 1-trans-tri-n-butylstannyl-4-dimethoxymethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-formyl-2-homo-13-trans prostene |
| 136 | 1-trans-tri-n-butylstannyl-4-fluoromethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-fluoromethyl-2-homo-13-trans prostene |
| 137 | 1-trans-tri-n-butylstannyl-4-difluoromethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-difluoromethyl-2-homo-13-trans prostene |
| 138 | 1-trans-tri-n-butylstannyl-4-trifluoromethyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-trifluoromethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 139 | 1-iodo-4-triphenylmethoxy-1-nonene | 2-(8,9-bis-trimethylsilyloxynonyl)cyclopent-2-en-1-one | dl-1,16-dihydroxy-1-hydroxymethyl-9-oxo-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 140 | 1-trans-tri-n-butylstannyl-4-methyl-4-trimethylsilyloxy-1-octene | 2-(8,9-bis-trimethylsilyloxynonyl)cyclopent-2-en-1-one | dl-1,16-dihydroxy-1-hydroxymethyl-9-oxo-16-methyl- |

| EXAMPLE | VINYL IODIDE | CYCLOPENTENONE | PRODUCT PROSTAGLANDIN OF THE 11-DEOXY PGE1 SERIES |
|---|---|---|---|
| 141 | 1-trans-tri-n-butylstannyl-4-trimethylsilyloxymethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-hydroxymethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 142 | 1-trans-iodo-4-triphenylmethoxy-1-octene | 2-(8,9-bis-trimethylsilyloxynonyl) cyclopent-2-en-1-one | dl-1,16-dihydroxy-1-hydroxymethyl-9-oxo-2-homo-13-trans prostene |
| EXAMPLE | VINYL TIN | CYCLOPENTENONE | PRODUCT PROSTAGLANDIN OF THE 11-DEOXY PGE1 SERIES |
| 143 | 1-trans-tri-n-butylstannyl-4-methyl-4-trimethylsilyloxy-1-octene | 2-(8,9-bis-trimethylsilyloxynonyl) cyclopent-2-en-1-one | dl-1,16-dihydroxy-1-hydroxymethyl-9-oxo-16-methyl-2-homo-13-trans prostene |
| 144 | 1-trans-tri-n-butylstannyl-4-chloromethyl-4-trimethylsilyloxy-1-octene | 2-(8,9-bis-trimethylsilyloxynonyl) cyclopent-2-en-1-one | dl-1,16-dihydroxy-1-hydroxymethyl-9-oxo-16-chloromethyl-2-homo-13-trans prostene |
| 145 | 1-trans-tri-n-butylstannyl-5-methyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-17-methyl-20-methyl-2-homo-13-trans prostene |
| 146 | 1-trans-tri-n-butylstannyl-4-vinyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-vinyl-20-methyl-2-homo-13-trans prostene |
| 147 | 1-trans-tri-n-butylstannyl-4-trimethylsilylethynyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-ethynyl-20-methyl-2-homo-13-trans prostene |
| 148 | 1-trans-tri-n-butylstannyl-5-methylene-4-triethylsilyloxy-1-nonene | 2-(8,9-bis-trimethylsilyloxynonyl) cyclopent-2-en-1-one | dl-1,16-dihydroxy-1-hydroxymethyl-9-oxo-17-methylene-20-methyl-2-homo-13-trans prostene |
| 149 | 1-trans-tri-n-butylstannyl-4-methyl-5-methylene-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-methyl-17-methylene-20-methyl-2-homo-13-trans prostene |
| 150 | 1-trans-tri-n-butylstannyl-4-dimethoxymethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-formyl-20-methyl-2-homo-13-trans prostene |
| 151 | 1-trans-tri-n-butylstannyl-4-fluoromethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-fluoromethyl-20-methyl-2-homo-13-trans prostene |
| 152 | 1-trans-tri-n-butylstannyl-4-difluoromethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-difluoromethyl-20-methyl-2-homo-13-trans prostene |
| 153 | 1-trans-tri-n-butylstannyl-4-trifluoromethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-trifluoromethyl-20-methyl-2-homo-13-trans prostene |
| 154 | 1-trans-tri-n-butylstannyl-4-chloromethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-chloromethyl-20-methyl-2-homo-13-trans prostene |
| 155 | 1-trans-tri-n-butylstannyl-4-trimethylsilyloxymethyl-4-trimethylsilyloxy-1-nonene | 2-(8,9-bis-trimethylsilyloxynonyl) cyclopent-2-en-1-one | dl-1,16-dihydroxy-1-hydroxymethyl-9-oxo-16-hydroxymethyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 156 | 1-trans-iodo-3-triphenylmethoxy-1-decene | 2-(8,9-bis-trimethylsilyloxynonyl) cyclopent-2-en-1-one | dl-1,15a-dihydroxy-1-hydroxymethyl-9-oxo-20-ethyl-2-homo-13-trans prostene |
| 157 | 1-trans-iodo-3-methyl-3-trimethylsilyloxy-1-decene | 2-(8,9-bis-trimethylsilyloxynonyl) cyclopent-2-en-1-one | dl-1,15a-dihydroxy-1-hydroxymethyl-9-oxo-15-methyl-20-ethyl-2-homo-13-trans prostene |
| 158 | 1-trans-iodo-4,4-dimethyl-3-trimethylsilyloxy-1-decene | 2-(8,9-bis-trimethylsilyloxynonyl) cyclopent-2-en-1-one | dl-1,15a-dihydroxy-1-hydroxymethyl-9-oxo-16,16-dimethyl-20-ethyl-2-homo-13-trans prostene |
| 159 | 1-trans-iodo-4,4-trimethylene-3-trimethylsilyloxy-1-decene | 2-(8,9-bis-trimethylsilyloxynonyl) cyclopent-2-en-1-one | dl-1,15a-dihydroxy-1-hydroxymethyl-9-oxo-16,16-trimethylene-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 160 | 1-trans-tri-n-butylstannyl-3-vinyl-3-trimethylsilyloxy-1-decene | 2-(8,9-bis-trimethylsilyloxynonyl) cyclopent-2-en-1-one | dl-1,15a-dihydroxy-1-hydroxymethyl-9-oxo-15-vinyl-20-ethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 161 | 1-trans-iodo-4-triphenylmethoxy-1-decene | 2-(8,9-bis-trimethylsilyloxynonyl) cyclopent-2-en-1-one | dl-1,16-dihydroxy-1-hydroxymethyl-9-oxo-20-ethyl-2-homo-13-trans prostene |

-continued

| EXAMPLE | VINYL TIN | CYCLOPENTENONE | PRODUCT PROSTAGLANDIN OF THE 11-DEOXY PGE1 SERIES |
|---|---|---|---|
| 162 | 1-trans-tri-n-butylstannyl-4-methyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-methyl-20-ethyl-2-homo-13-trans prostene |
| 163 | 1-trans-tri-n-butylstannyl-5-methyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-17-methyl-20-ethyl-2-homo-13-trans prostene |
| 164 | 1-trans-tri-n-butylstannyl-4-vinyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-vinyl-20-ethyl-2-homo-13-trans prostene |
| 165 | 1-trans-tri-n-butylstannyl-4-trimethylsilylethynyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-ethynyl-20-ethyl-2-homo-13-trans prostene |
| 166 | 1-trans-tri-n-butylstannyl-5-methylene-4-trimethylsilyloxy-1-decene | 2-(8,9-bis-trimethylsilyloxynonyl)cyclopent-2-en-1-one | dl-1,16-dihydroxy-1-hydroxymethyl-9-oxo-17-methylene-20-ethyl-2-homo-13-trans prostene |
| 167 | 1-trans-tri-n-butylstannyl-4-methyl-5-methylene-4-triethylsilyloxy-1-decene | 2-(8,9-bis-trimethylsilyloxynonyl)cyclopent-2-en-1-one | dl-1,16-dihydroxy-1-hydroxymethyl-9-oxo-16-methyl-17-methylene-20-ethyl-2-homo-13-trans prostene |
| 168 | 1-trans-tri-n-butylstannyl-4-dimethoxymethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-formyl-20-ethyl-2-homo-13-trans prostene |
| 169 | 1-trans-tri-n-butylstannyl-4-fluoromethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-fluoromethyl-20-ethyl-2-homo-13-trans prostene |
| 170 | 1-trans-tri-n-butylstannyl-4-difluoromethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-difluoromethyl-20-ethyl-2-homo-13-trans prostene |
| 171 | 1-trans-tri-n-butylstannyl-4-trifluoromethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-trifluoromethyl-20-ethyl-2-homo-13-trans prostene |
| 172 | 1-trans-tri-n-butylstannyl-4-chloromethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-chloromethyl-20-ethyl-2-homo-13-trans prostene |
| 173 | 1-trans-tri-n-butylstannyl-4-trimethylsilyloxymethyl-4-trimethylsilyloxy-1-decene | 2-(8,9-bis-trimethylsilyloxynonyl)cyclopent-2-en-1-one | dl-1,16-dihydroxy-1-hydroxymethyl-9-oxo-16-hydroxymethyl-20-ethyl-2-homo-13-trans prostene |
| 174 | 1-trans-tri-n-butylstannyl-4-methyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-methyl-20-nor-2-nor-13-trans prostene |
| 175 | 1-trans-tri-n-butylstannyl-4-ethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-16-ethyl-2-nor-13-trans prostene |
| 176 | 1-trans-tri-n-butylstannyl-5-methyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-17-methyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 177 | 1-trans-iodo-5,5-dimethyl-4-trimethylsilyloxy-1-octene | 2-(6,7-bis-trimethylsilyloxyheptyl)cyclopent-2-en-1-one | dl-1,16-dihydroxy-1-hydroxymethyl-9-oxo-17,17-dimethyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 178 | 1-trans-tri-n-butylstannyl-4-vinyl-4-trimethylsilyloxy-1-heptene | 2-(6,7-bis-trimethylsilyloxyheptyl)cyclopent-2-en-1-one | dl-1,16-dihydroxy-1-hydroxymethyl-9-oxo-16-vinyl-20-nor-2-nor-13-trans prostene |

The PGE compounds of this invention also have bronchodilator activity as determined in a test using dogs anestheti artificially ventilated and submitted to a continuous respiratory spasm induced by pilocarpine.

EXAMPLE 179

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, *J. Appl. Physiol.*, 19, 360 (1964)]. All the measurements are made with the dogs positioned supine in a heated, V-shaped table. Curazation is obtained by succinylcholine chloride using a starting injection of 3 mg/Kg lasting 3 minutes, followed by a continuous perfusion of 0.1 mg/Kg/minute.

The respiratory spasm is induced by a starting injection of 400 µg/Kg of pilocarpine HCl lasting 5 minutes. An increase or decrease in the dose of pilocarpine HCl may occur as a function of the observed effect on the airway's resistance A 15 minute delay is observed before the start of a continuous perfusion of pilocarpine HCl at a dose of 4 µg/Kg/minute to maintain a constant spasm during the test.

A metallic cannula is inserted and fixed, after the cheotomy, into the upper part of the trachea. The two cephallic veins and the two femoral veins are catheterized to inject various agents. The femoral artery is catheterized to measure the systemic blood pressure. An esophageal balloon (11 cm × 2.5 cm) is inserted into the lower third of the oesophagus to measure the endothoracic pressure. The measurement of a flow is made with a Fleish pneumotachograph connected to the tracheal tube.

The transpulmonary pressure is measured as follows. The tracheal cannula is equipped with a stainless steel axial tube (1.5 mm) which is closed at its distal end and projected 2.5 cm beyond the end of the cannula. Three holes with a diameter of one mm are pierced on this latter segment. This tube which is used to measure the tracheal pressure, is connected to one of the two chambers of a Sanborn 267 B/C differential transducer. The other chamber is connected to the esophageal balloon by means of a polyethylene catheter of the same length and characteristics as the balloon's.

The airflow is measured from the Fleish pneuomotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope [Mead and Whittenberger, *J. Appl. Physiol.*, 5,779 (1953)].

The value of the pulmonary elastance, expressed in cm of water/liter, is obtained by means of the same principle, i.e., an electrical signal proportioned to the volume is subtracted from the transpulmonary pressure signal, in order to optimize the pressure-flow loop on the oscilloscope.

The details of this method are described by Lulling, et al. [*Med. Pharmacol. Exp.*, 16, 481 (1967)].

| Compound | KONZETT DATA | | |
|---|---|---|---|
| | 5-HT (ED$_{50}$ g/kg) | Hist (ED$_{50}$ g/kg) | Ach (ED$_{50}$ g/kg) |
| dl-1,11,15-trihydroxymethyl-9-oxo-15-methyl-5-cis-13-trans prostadiene | $8.3 \times 10^{-3}$ | $750 \times 10^{-6}$ | $4.3 \times 10^{-3}$ |
| dl-1,11,16-trihydroxy-1-hydroxymethyl-9-oxo-16-methyl-5-cis-13-trans prostadiene | $20 \times 10^{-3}$ | $43 \times 10^{-3}$ | $331 \times 10^{-3}$ |
| dl-1,11,16-trihydroxy-1-hydroxymethyl-9-oxo-16-vinyl-5-cis-13-trans-prostadiene | $7.4 \times 10^{-3}$ | $6.8 \times 10^{-3}$ | $11.8 \times 10^{-3}$ |
| dl-1,11,16-trihydroxy-1-hydroxymethyl-9-oxo-16-methyl-13-trans-prostene | $16.2 \times 10^{-3}$ | $12.2 \times 10^{-3}$ | $75.9 \times 10^{-3}$ |
| dl-1,11,16-trihydroxy-1-hydroxymethyl-9-oxo-16-vinyl-13-trans-prostene | $22.1 \times 10^{-3}$ | $15.5 \times 10^{-3}$ | $20.1 \times 10^{-3}$ |

We claim:

1. Compounds of the formula:

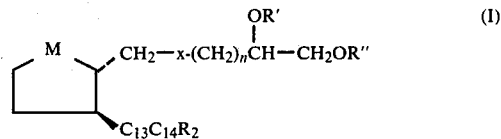

n is the integer 3-5 inclusive; wherein M is the divalent moiety selected from the group

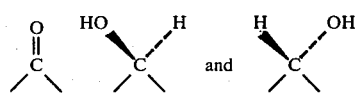

X is —CH₂CH₂—, and; R' and R" are the same or different and are hydrogen, $C_1$ to $C_4$ alkyl, $C_1$ to $C_6$ alkanoyl or optionally substituted benzoyl, the substituents selected from the group $C_1$ to $C_4$ alkoxy, halo and trifluoromethyl; $C_{13}$–$C_{14}$ is selected from the group —CH=CH—(trans) and —CH₂CH₂—; and $R_2$ is selected from the group

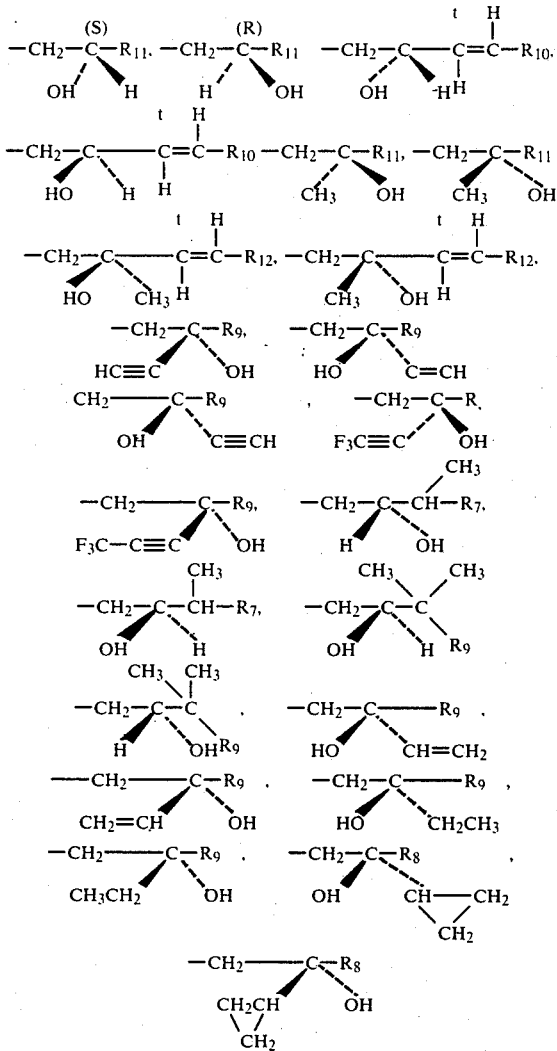

$R_7$ is selected from the group consisting of $C_2$–$C_4$ alkyl;
$R_8$ is selected from the group consisting of $C_1$–$C_2$ alkyl;
$R_9$ is selected from the group consisting of $C_3$–$C_6$ alkyl;
$R_{10}$ is selected from the group consisting of $C_1$–$C_4$ alkyl;
$R_{11}$ is selected from the group consisting of $C_3$–$C_7$ alkyl;
$R_{12}$ is selected from the group consisting of $C_1$ to $C_4$ alkyl the racemic mixtures thereof; and the mirror images thereof, and the pharmaceutically acceptable, non-toxic salts thereof.

2. A racemic compound according to claim 1, dl-1,16-DIHYDROXY-1-HYDROXYMETHYL-9-OXO-16-ETHYL-13-trans PROSTENE.

3. A racemic compound according to claim 1, dl-1,16a-DIHYDROXY-1-HYDROXYMETHYL-9-OXO-16-ETHYL-13-trans PROSTENE.

4. A racemic compound according to claim 1, dl-1,16B-DIHYDROXY-1-HYDROXYMETHYL-9-OXO-16-ETHYL-13-trans PROSTENE.

5. A racemic compound according to claim 1, dl-1,16-DIHYDROXY-1-HYDROXYMETHYL-9-OXO-17-METHYL-13-trans PROSTENE.

6. A racemic compound according to claim 1, dl-1,16a-DIHYDROXY-1-HYDROXYMETHYL-9-OXO-17-METHYL-13-trans PROSTENE.

7. A racemic compound according to claim 1, dl-1,16B-DIHYDROXY-1-HYDROXYMETHYL-9-OXO-17-METHYL-13-trans PROSTENE.

8. A racemic compound according to claim 1, dl-1,16-DIHYDROXY-1-HYDROXYMETHYL-9-OXO-17,17-DIMETHYL-13-trans PROSTENE.

9. A racemic compound according to claim 1, dl-1,16a-DIHYDROXY-1-HYDROXYMETHYL-9-OXO-17,17-DIMETHYL-13-trans PROSTENE.

10. A racemic compound according to claim 1, dl-1,16B-DIHYDROXY-1-HYDROXYMETHYL-9-OXO-17,17-DIMETHYL-13-trans PROSTENE.

11. A racemic compound according to claim 1, dl-1,16-DIHYDROXY-1-HYDROXYMETHYL-9-OXO-16-VINYL-13-trans PROSTENE.

12. A racemic compound according to claim 1, dl-1,16a-DIHYDROXY-1-HYDROXYMETHYL-9-OXO-16-VINYL-13-trans PROSTENE.

13. A racemic compound according to claim 1, dl-1,16B-DIHYDROXY-1-HYDROXYMETHYL-9-OXO-16-VINYL-13-trans PROSTENE.

14. A racemic compound according to claim 1, dl-1,16-DIHYDROXY-1-HYDROXYMETHYL-9-OXO-16-CYCLOPROPYL-13-trans PROSTENE.

15. A racemic compound according to claim 1, dl-1,16a-DIHYDROXY-1-HYDROXYMETHYL-9-OXO-16-CYCLOPROPYL-13-trans PROSTENE.

16. A racemic compound according to claim 1, dl-1,16B-DIHYDROXY-1-HYDROXYMETHYL-9-OXO-16-CYCLOPROPYL-13-trans PROSTENE.

17. A racemic compound according to claim 1, dl-1,16-DIHYDROXY-1-HYDROXYMETHYL-9-OXO-16-ETHYNYL-13-trans PROSTENE.

18. A racemic compound according to claim 1, dl-1,16a-DIHYDROXY-1-HYDROXYMETHYL-9-OXO-16-ETHYNYL-13-trans PROSTENE.

19. A racemic compound according to claim 1, dl-1,16B-DIHYDROXY-1-HYDROXYMETHYL-9-OXO-16-ETHYNYL-13-trans PROSTENE.

20. A racemic compound according to claim 1, dl-1,16-DIHYDROXY-1-HYDROXYMETHYL-9-OXO-17-METHYLENE-13-trans PROSTENE.

21. A racemic compound according to claim 1, dl-1,16a-DIHYDROXY-1-HYDROXYMETHYL-9-OXO-17-METHYLENE-13-trans PROSTENE.

22. A racemic compound according to claim 1, dl-1,16B-DIHYDROXY-1-HYDROXYMETHYL-9-OXO-17-METHYLENE-13-trans PROSTENE.

23. A racemic compound according to claim 1, dl-1,16-DIHYDROXY-1-HYDROXYMETHYL-9-OXO-16-METHYL-17-METHYLENE-13-trans PROSTENE.

24. A racemic compound according to claim 1, dl-1,16a-DIHYDROXY-1-HYDROXYMETHYL-9-OXO-16-METHYL-17-METHYLENE-13-trans PROSTENE.

25. A racemic compound according to claim 1, dl-1,16B-DIHYDROXY-1-HYDROXYMETHYL-9-OXO-16-METHYL-17-METHYLENE-13-trans PROSTENE.

26. A racemic compound according to claim 1, dl-1,16-DIHYDROXY-1-HYDROXYMETHYL-9-OXO-16-FORMYL-13-trans PROSTENE.

27. A racemic compound according to claim 1, dl-1,16a-DIHYDROXY-1-HYDROXYMETHYL-9-OXO-16-FORMYL-13-trans PROSTENE.

28. A racemic compound according to claim 1, dl-1,16B-DIHYDROXY-1-HYDROXYMETHYL-9-OXO-16-FORMYL-13-trans PROSTENE.

29. A racemic compound according to claim 1, dl-1,16-DIHYDROXY-1-HYDROXYMETHYL-9-OXO-16-FLUOROMETHYL-13-trans PROSTENE.

30. A racemic compound according to claim 1, dl-1,16a-DIHYDROXY-1-HYDROXYMETHYL-9-OXO-16-FLUOROMETHYL-13-trans PROSTENE.

31. A racemic compound according to claim 1, dl-1,16B-DIHYDROXY-1-HYDROXYMETHYL-9-OXO-16-FLUOROMETHYL-13-trans PROSTENE.

32. A racemic compound according to claim 1, dl-1,16-DIHYDROXY-1-HYDROXYMETHYL-9-OXO-16-DIFLUOROMETHYL-13-trans PROSTENE.

33. A racemic compound according to claim 1, dl-1,16a-DIHYDROXY-1-HYDROXYMETHYL-9-OXO-16-DIFLUOROMETHYL-13-trans PROSTENE.

34. A racemic compound according to claim 1, dl-1,16B-DIHYDROXY-1-HYDROXYMETHYL-9-OXO-16-DIFLUOROMETHYL-13-trans PROSTENE.

35. A racemic compound according to claim 1, dl-1,16-DIHYDROXY-1-HYDROXYMETHYL-9-OXO-16-TRIFLUOROMETHYL-13-trans PROSTENE.

36. A racemic compound according to claim 1, dl-1,16a-DIHYDROXY-1-HYDROXYMETHYL-9-OXO-16-TRIFLUOROMETHYL-13-trans PROSTENE.

37. A racemic compound according to claim 1, dl-1,16B-DIHYDROXY-1-HYDROXYMETHYL-9-OXO-16-TRIFLUOROMETHYL-13-trans PROSTENE.

38. A racemic compound according to claim 1, dl-1,16-DIHYDROXY-1-HYDROXYMETHYL-9-OXO-16-CHLOROMETHYL-13-trans PROSTENE.

39. A racemic compound according to claim 1, dl-1,16a-DIHYDROXY-1-HYDROXYMETHYL-9-OXO-16-CHLOROMETHYL-13-trans PROSTENE.

40. A racemic compound according to claim 1, dl-1,16B-DIHYDROXY-1-HYDROXYMETHYL-9-OXO-16-CHLOROMETHYL-13-trans PROSTENE.

41. A racemic compound according to claim 1, dl-1,16-DIHYDROXY-1-HYDROXYMETHYL-9-OXO-16-HYDROXYMETHYL-13-trans PROSTENE.

42. A racemic compound according to claim 1, dl-1,16a-DIHYDROXY-1-HYDROXYMETHYL-9-OXO-16-HYDROXYMETHYL-13-trans PROSTENE.

43. A racemic compound according to claim 1, dl-1,16B-DIHYDROXY-1-HYDROXYMETHYL-9-OXO-16-HYDROXYMETHYL-13-trans PROSTENE.

44. A racemic compound according to claim 1, dl-1,16-DIHYDROXY-1-HYDROXYMETHYL-9-OXO-16-METHYL-19-CHLORO-20-nor-13-trans PROSTENE.

45. A racemic compound according to claim 1, dl-1,16a-DIHYDROXY-1-HYDROXYMETHYL-9-OXO-16-METHYL-19-CHLORO-20-nor-13-trans PROSTENE.

46. A racemic compound according to claim 1, dl-1,16B-DIHYDROXY-1-HYDROXYMETHYL-9-OXO-16-METHYL-19-CHLORO-20-nor-13-trans PROSTENE.

47. A racemic compound according to claim 1, dl-1,16-DIHYDROXY-1-HYDROXYMETHYL-9-OXO-13-trans PROSTENE.

48. A racemic compound according to claim 1, dl-1,16a-DIHYDROXY-1-HYDROXYMETHYL-9-OXO-13-trans PROSTENE.

49. A racemic compound according to claim 1, dl-1,16B-DIHYDROXY-1-HYDROXYMETHYL-9-OXO-13-trans PROSTENE.

50. A racemic compound according to claim 1, dl-1,16-DIHYDROXY-1-HYDROXYMETHYL-9-OXO-16-METHYL-13-trans PROSTENE.

51. A racemic compound according to claim 1, dl-1,16a-DIHYDROXY-1-HYDROXYMETHYL-9-OXO-16-METHYL-13-trans PROSTENE.

52. A racemic compound according to claim 1, dl-1,16B-DIHYDROXY-1-HYDROXYMETHYL-9-OXO-16-METHYL-13-trans PROSTENE.

* * * * *